(12) United States Patent
Hoffman et al.

(10) Patent No.: US 6,337,314 B1
(45) Date of Patent: *Jan. 8, 2002

(54) MAMMALIAN-DERIVED PEPTIDES FOR THE TREATMENT OF MICROBIAL INFECTIONS

(75) Inventors: Brian F. Hoffman, Key Biscayne, FL (US); Bernard Dubnick, Old Tappan, NJ (US)

(73) Assignee: Theragem, Inc., OldTappan, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/352,078

(22) Filed: Jul. 14, 1999

Related U.S. Application Data

(63) Continuation of application No. PCT/US98/16746, filed on Aug. 10, 1998.
(60) Provisional application No. 60/061,454, filed on Oct. 8, 1997.

(51) Int. Cl.[7] .................... A61K 31/74; A61K 35/14; A61K 38/00

(52) U.S. Cl. ................ 514/2; 514/6; 514/12; 514/21; 530/324; 530/380; 530/385; 530/386; 530/827; 530/829; 424/78.07; 424/529; 424/530

(58) Field of Search ............... 514/2, 6, 12, 21; 530/324, 380, 385, 386, 827, 829; 424/78.07, 529, 530

(56) References Cited

U.S. PATENT DOCUMENTS

| | | | |
|---|---|---|---|
| 5,239,061 A | 8/1993 | Fronticelli et al. | 530/385 |
| 5,370,869 A | 12/1994 | Shanbrom | 424/78.22 |
| 5,380,664 A | 1/1995 | Carver et al. | 436/10 |

FOREIGN PATENT DOCUMENTS

| | | | |
|---|---|---|---|
| JP | 05305126 | | 11/1993 |
| WO | WO93/08831 | * | 5/1993 |

OTHER PUBLICATIONS

Perutz, M.F., et al., Nature, 291: 682–684, Jun. 25, 1981.
Hobson, D. et al., J. of Exp. Med. 107(2): 167–183 (1958).
Wood, D.C. et al., Laborat. Invest., 7(1):1–8 (1958).
Karelin, A.A., et al., Peptides, 16(4): 693–7 (1995).
Nicolas, P. et al., Annu. Rev. Microbiol., 49:277–304, 1995.
International Search Report for PCT/US98/16746 dated Oct. 29, 1998.
Ivanov, V.T. et al., *Pure & Appl. Chem.*, 70(1):67–74, 1998.
Fruitier, I. et al., *FEBS Letters*, 447:81–86, 1999.
Ivanov, V.T. et al., *Biopoly*, 43:171–188, 1997.
Karelin, A.A. et al., *FEBS Letters*, 428:7–12, 1998.
Blishchenko, E.Y. et al., *Biochem. and Biophys. Res. Comm.*, 224:721–727, 1996.
Blishchenko, E.Y. et al., *Peptides*, 18(1):79–85, 1997.
Yatskin, O.N. et al., *FEBS Letters*, 428:286–290, 1998.

* cited by examiner

Primary Examiner—Christopher S. F. Low
Assistant Examiner—Abdel A. Mohamed
(74) Attorney, Agent, or Firm—Darby & Darby

(57) ABSTRACT

The present invention provides compositions useful as antimicrobial agents which include mammalian hemoglobin, the α and β chains of hemoglobin free of heme, fragments of the α and β chains that result from cyanogen bromide cleavage of the α and β chains, and synthetic peptides derived therefrom. The compositions exert antimicrobial activity against both bacteria and fungi that is comparable to known antimicrobial peptides from human neutrophils, cathepsin G and azurocidin. Sensitive organisms include Gram-negative bacteria such as *Escherichia coli* and *Pseudomonas aeruginosa*, Gram-positive bacteria such as *Staphylococcus aureus* and *Streptococcus faecalis*, and the fungus *Candida albicans*. Methods for preparing the compositions also are provided.

25 Claims, 15 Drawing Sheets

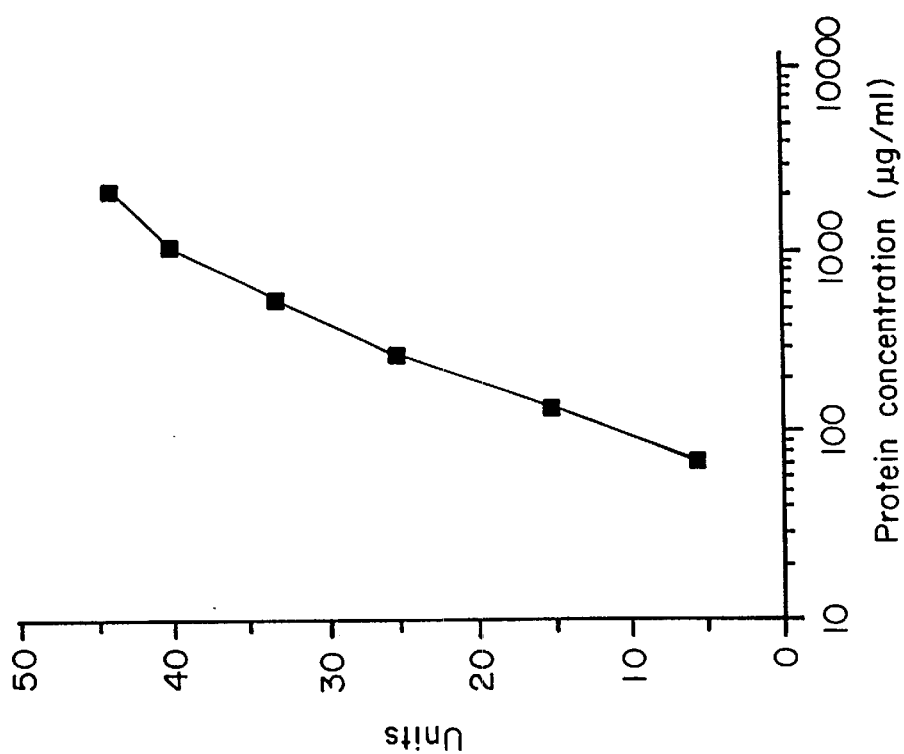
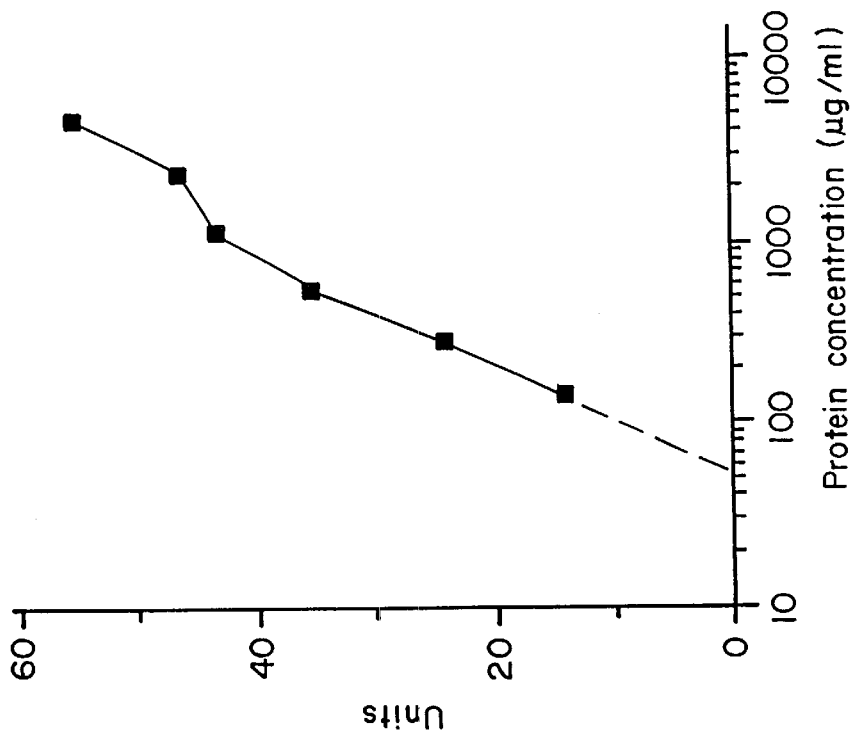

Protein concentration (μg/ml)

MAMMALIAN-DERIVED PEPTIDES FOR THE TREATMENT OF MICROBIAL INFECTIONS

This is a continuation of application Ser. No. PCT/US98/16746, filed Aug. 10, 1998, which claims priority of U.S. Provisional Application Serial No. 60/061,454, filed Oct. 8, 1997. Each of these prior applications is hereby incorporated herein by reference, in its entirety.

The present application claims the benefit of U.S. Provisional Application Ser. No. 60/061,454 filed Oct. 8, 1997, the entire disclosure of which is incorporated herein by reference.

FIELD OF THE INVENTION

The present invention relates to a method for treating microbial infections of mammals, including humans and other primates; a method for killing bacteria and fungi; and a method for treating material subject to microbial contamination by administration of an effective antimicrobial amount of hemoglobin, or of the α or β chains of this molecule, free of heme, or polypeptide fragments of the α and β chains resulting from cleavage by cyanogen bromide or synthetic fragments thereof. The invention also relates to compositions comprising such proteins, polypeptides or fragments.

BACKGROUND OF THE INVENTION

Antibacterial peptides from natural sources have a long history. In 1939 Dubos demonstrated that a soil bacillus, subsequently identified as *B. brevis*, produced substances that could prevent pneumococcal infections in mice. Subsequently, Hotchkiss and Dubos purified two substances composed of amino acids and one of these, gramicidin, became available as a therapeutic agent. Subsequent studies on antimicrobial peptides have identified many active agents (1). (Within this application several publications are referenced by Arabic numerals within parentheses. Full citations for these references, listed in sequence, may be found at the end of the specification. All of these references and any additional references cited within this application are herein incorporated by reference in their entirety.)

Many bacteria produce antimicrobial peptides (bacteriocins) and proteins; those released from Gram-negative bacteria are the more potent and have the wider spectrum of activity (2). The defensins are small antimicrobial peptides found in neutrophils, non-human macrophages and Paneth cells (3). Amphibian skin is a rich source of antimicrobial peptides, one of these, magainin, isolated from *Xenopus laevis*, currently is undergoing clinical trial (4,5). Plants form a variety of gene-encoded antimicrobial peptides including the phytoalexins, the PR proteins and the AMPs (6,7). Insects have been shown to synthesize bacteriocidal peptides and proteins such as cecropin obtained from the moth Cecropia (8,9,10) and the sarcotoxins obtained from the larvae of the flesh fly *Sarcocphaga perigrina* (11). The hemocytes of the horse-shoe crab Limulus are the source of the tachyplesins and squalamine, an aminosteroid with antimicrobial activity, has been isolated from the shark, *Squalus acanthias* (12).

Thus, many antimicrobial substances lie within the families of "natural" antibiotics such as the cecropins, magainins, defensins, serprocidins and others. These substances are widely distributed in nature and provide an innate defense mechanism against infection in species ranging from insects to amphibians to mammals. Generally these substances are stored in cells, to be induced and secreted within the animal when challenged. Many act by disrupting the bacterial cell membrane selectively; many would be toxic to host cells as well, were they not sequestered (13). A number of these compounds have been proposed as being useful as antimicrobial agents (14,15).

Hemoglobin (MW=64,500) consists of four polypeptide chains and four heme prosthetic groups in which the iron atoms are in the ferrous state. Heme is a metal complex consisting of an iron atom at the center of a porphyrin structure. The protein, called globin, consists of two α chains and two β chains. In the human there are two α chains each containing 141 amino acid residues and two β chains each containing 146 residues. The amino acid sequence of the α and β chains of human hemoglobin, is as follows:

| α chain | | | (SEQ ID NO:10) |
|---|---|---|---|
| 1           15 | 16           30 | 31           45 |
| VLSPADKTNVKAAWG | KVGAHAGEYGAEALE | RMFLSFPTTKTYFPH |
| 46           60 | 61           75 | 76           90 |
| FDLSHGSAQVKGHGK | KVADALTNAVAHVDD | MPNALSALSDLHAHK |
| 91          105 | 106         120 | 121         135 |
| LRVDPVNFKLLSHCL | LVTLAAHLPAEFTPA | VHASLDKFLASVSTV |
| 136 |
| LTSKYR |

| β chain | | | (SEQ ID NO:1) |
|---|---|---|---|
| 1           15 | 16           30 | 31           45 |
| VHLTPEEKSAVTALW | GKVNVDEVGGEALGR | LLVVYPWTQRFFESF |
| 46           60 | 61           75 | 76           90 |
| GDLSTPDAVMGNPKV | KAHGKKVLGAFSDGL | AHLDNLKGTFATLSE |
| 91          105 | 106         120 | 121         135 |
| LHCDKLHVDPENFRL | LGNVLVCVLAHHFGK | EFTPPVQAAYQKVVA |
| 136      146 |
| GVANALAHKYH |

The structure of heme (ferroprotoporphyrin IX) is well known.

One heme group is bound to each polypeptide chain through a coordination bond between the iron atom and the R group of a histidine residue. The sixth coordination bond of the iron atom is available to bind oxygen. In addition, hemoglobin also transports $H^+$, $CO_2$, and NO. The structure of heme is identical in all animals that have hemoglobin but the sequence of the globin chains varies considerably. In spite of this variation, the configuration of the tetramer is quite similar among species.

The interactions of hemoglobin with oxygen and carbon dioxide depend on the state of the heme and the residues surrounding it, as well as on regulation by heterotrophic ligands including $H^+$, $Cl^-$, $CO_2$, $HCO_3^-$ and 2,3, diphosphoglycerate. These ligands regulate the equilibrium between the high affinity state (the relaxed or R structure), and the low affinity tense state (or T structure). The stereochemistry of hemoglobin has been reviewed extensively (16,17).

Hemoglobin-based compositions have been developed for administration as blood substitutes. (18,19) These include chemically modified hemoglobin which contains the oxygencarrying heme group required for proper oxygen transport. While such modified hemoglobin-based compounds have been administered as blood substitutes, administration of unmodified hemoglobin, its heme free subunits or fragments or synthetic peptides therefrom has not previously been disclosed for this purpose or for other therapeutic uses. Indeed, the heme free α and β subunits would not be utilized for the purpose of providing blood substitutes, as they are incapable of binding oxygen.

SUMMARY OF THE INVENTION

The present invention provides a method for killing bacteria or fungi comprising contacting the bacteria or fungi with an antimicrobially effective amount of mammalian hemoglobin protein, hemoglobin protein fragment or polypeptide fragments thereof selected from the group consisting of intact hemoglobin, heme-free hemoglobin a chain, heme-free hemoglobin β chain, a hemoglobin α-3 fragment, a hemoglobin β-2 fragment, an amino acid sequence of SEQ ID NO: 3, an amino acid sequence of SEQ ID NO: 2, an amino acid sequence of SEQ ID NO: 5, an amino acid sequence of SEQ ID NO: 6, fragments of said proteins or polypeptide fragments thereof and combinations thereof.

The invention also provides a method for treating a subject having a bacterial or fungal infection comprising administering an antimicrobially effective amount of said protein, polypeptides and/or fragment compositions, a method for treating material subject to bacterial or fungal contamination comprising applying to or admixing with said material an antimicrobially effective amount of said compositions, and is directed to the use of said compositions for antimicrobial treatment of bacteria or fungi.

The invention additionally provides a pharmaceutical dosage form comprising an antimicrobially effective amount of said protein, polypeptide and/or fragment compositions and a pharmaceutically acceptable carrier, as well as providing a polypeptide of an amino acid sequence of SEQ ID NO: 5, an amino acid sequence of SEQ ID NO: 6 and fragments of said sequences.

BRIEF DESCRIPTION OF THE DRAWINGS

FIG. 11: Activity of beta chain against *Pseudomonas aeruginosa* at pH 5.5.

FIG. 12: Activity of beta chain against *Pseudomonas aeruginosa* at pH 5.5.

DETAILED DESCRIPTION OF THE INVENTION

Figure 2:
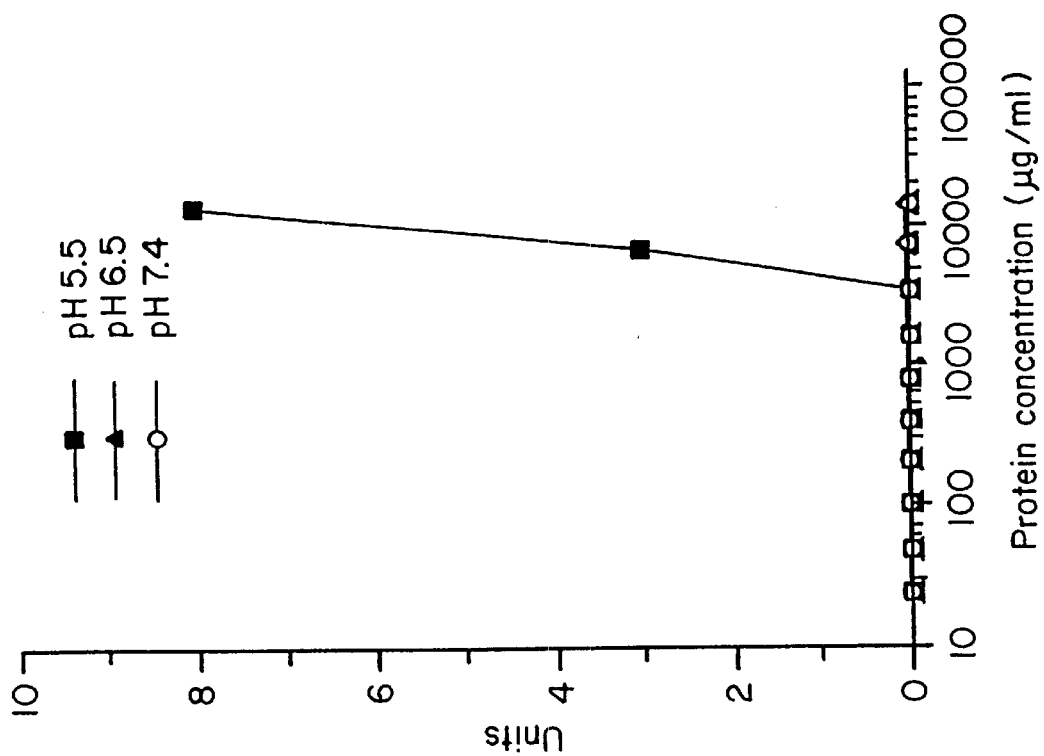
FIG. 2: Activity of hemoglobin against *Streptococcus faecalis* at three values of pH
Figure 1:
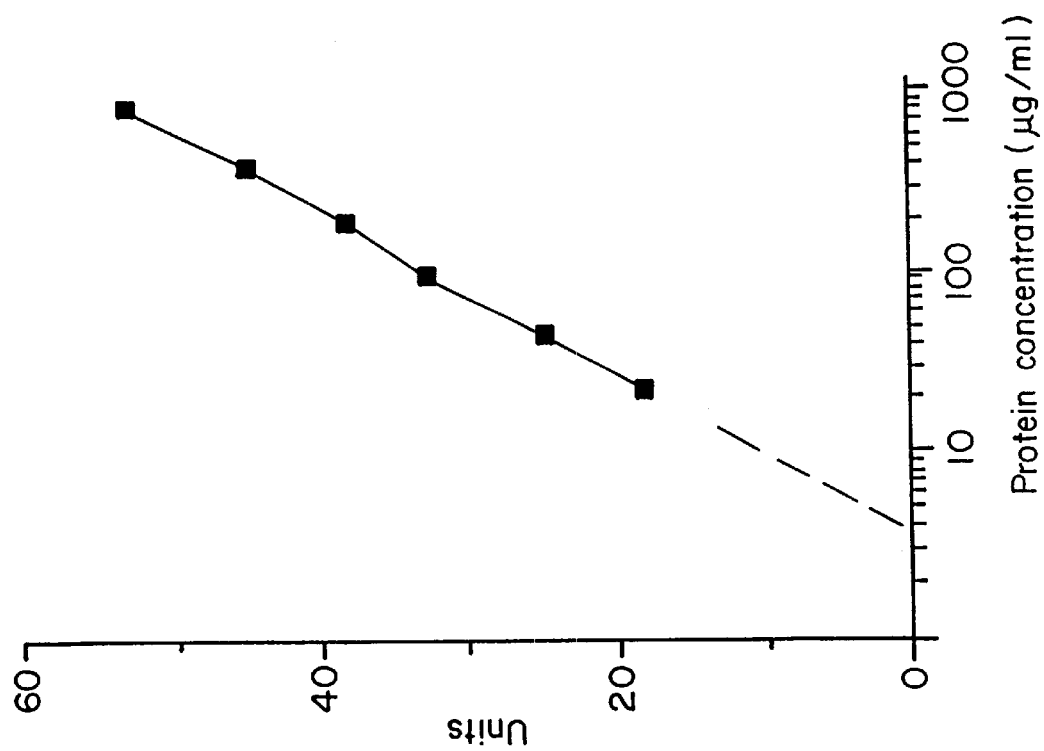
FIG. 1: Activity of hemoglobin against *Staphylococcus aureus* at pH 5.5.
Figure 4:
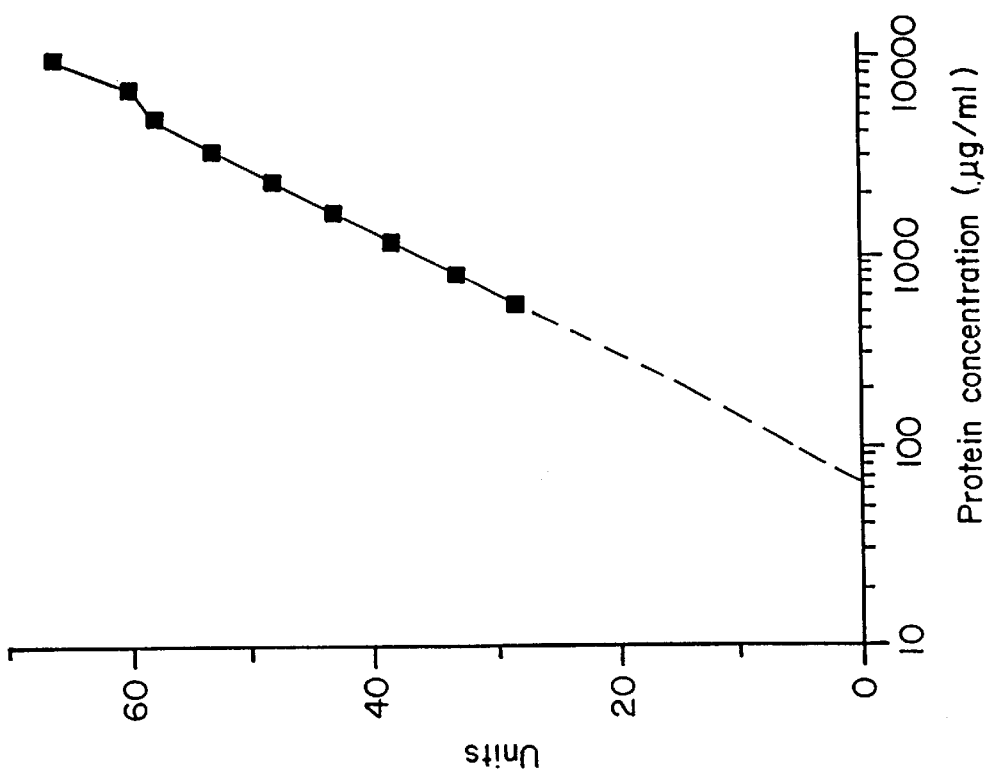
FIG. 4: Activity of hemoglobin against *Candida albicans* at pH 5.5.
Figure 3:
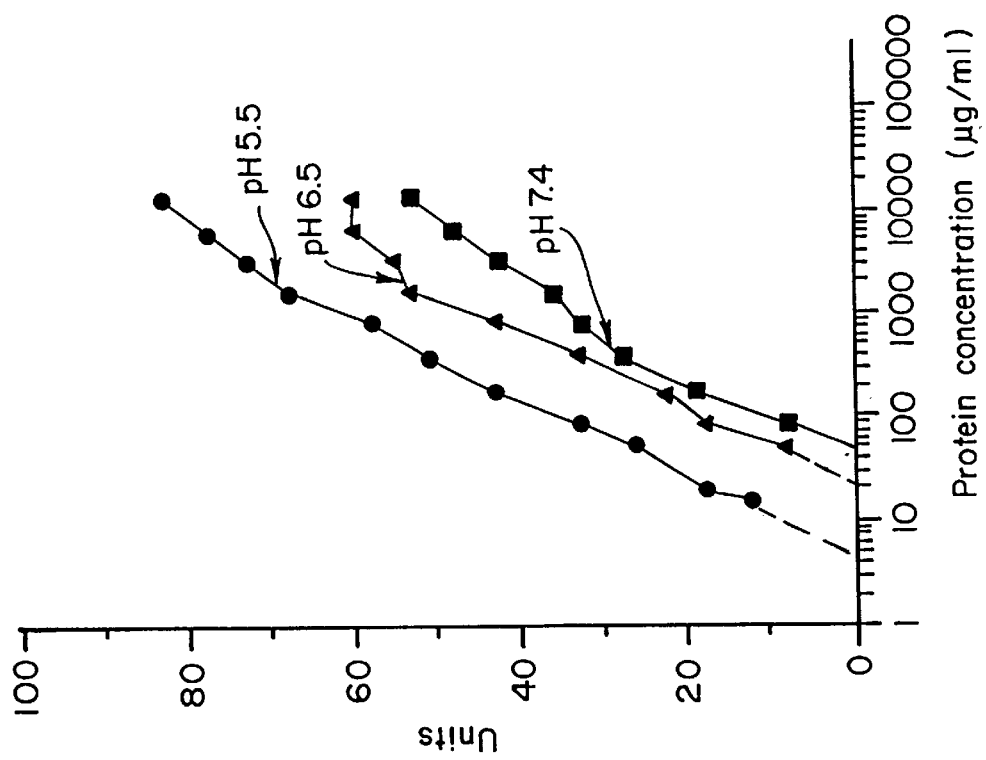
FIG. 3: Activity of hemoglobin against *Pseudomonas aeruginosa* at three values of pH
Figure 6:
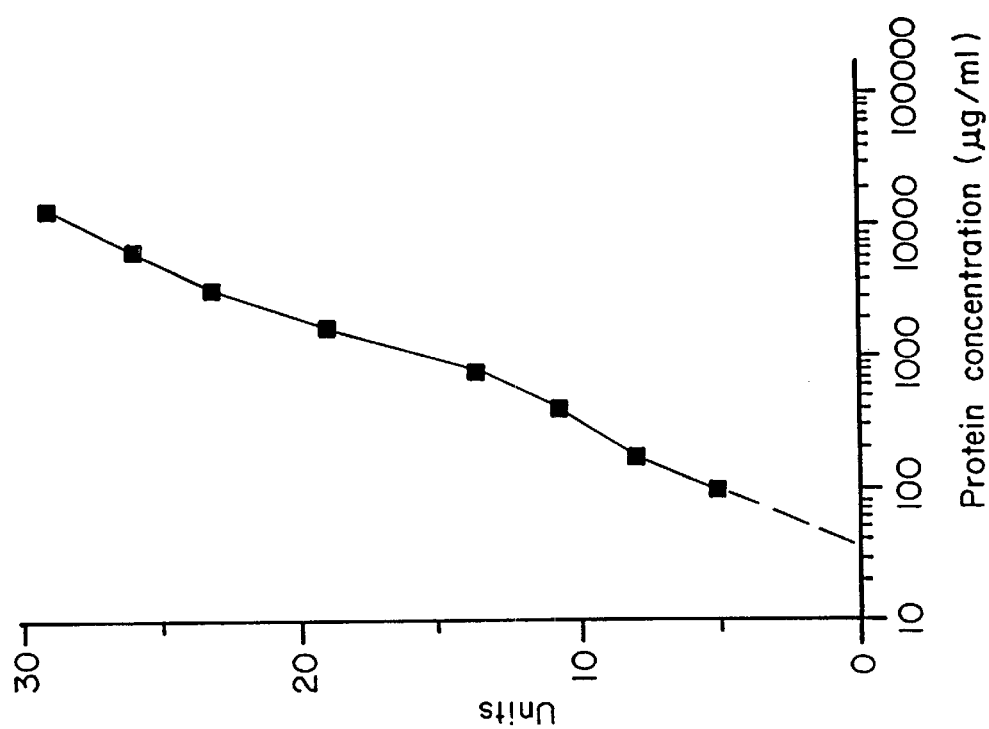
FIG. 6: Activity of hemoglobin against *Escherichia coli* at pH 7.4.
Figure 5:
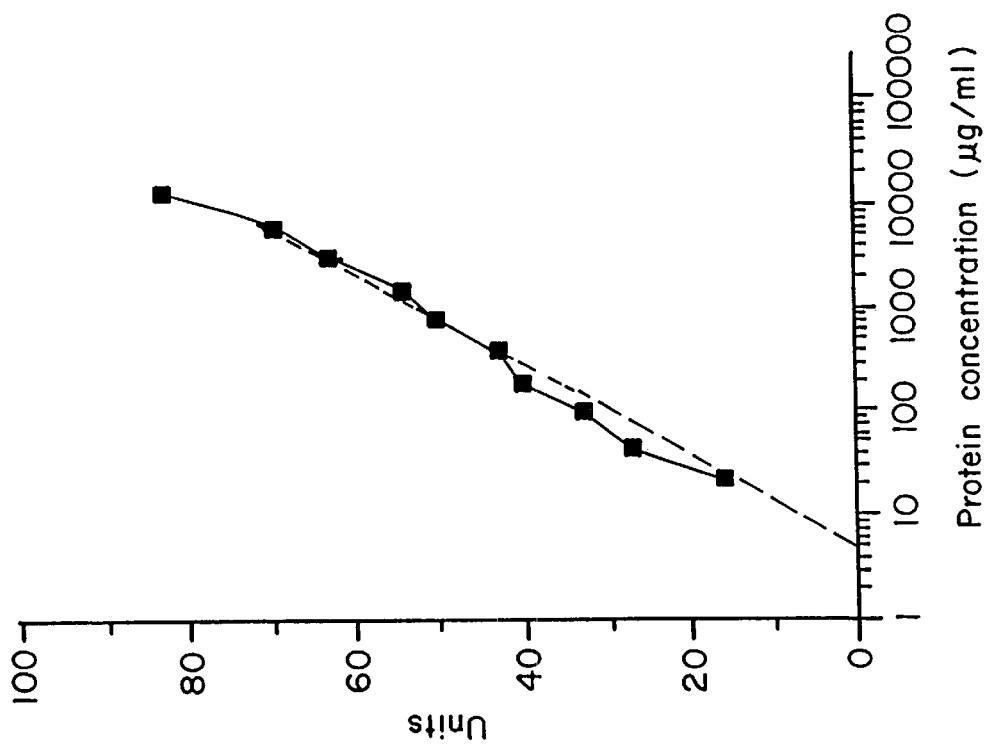
FIG. 5: Activity of hemoglobin against *Escherichia coli* at pH 5.5.
Figure 8:
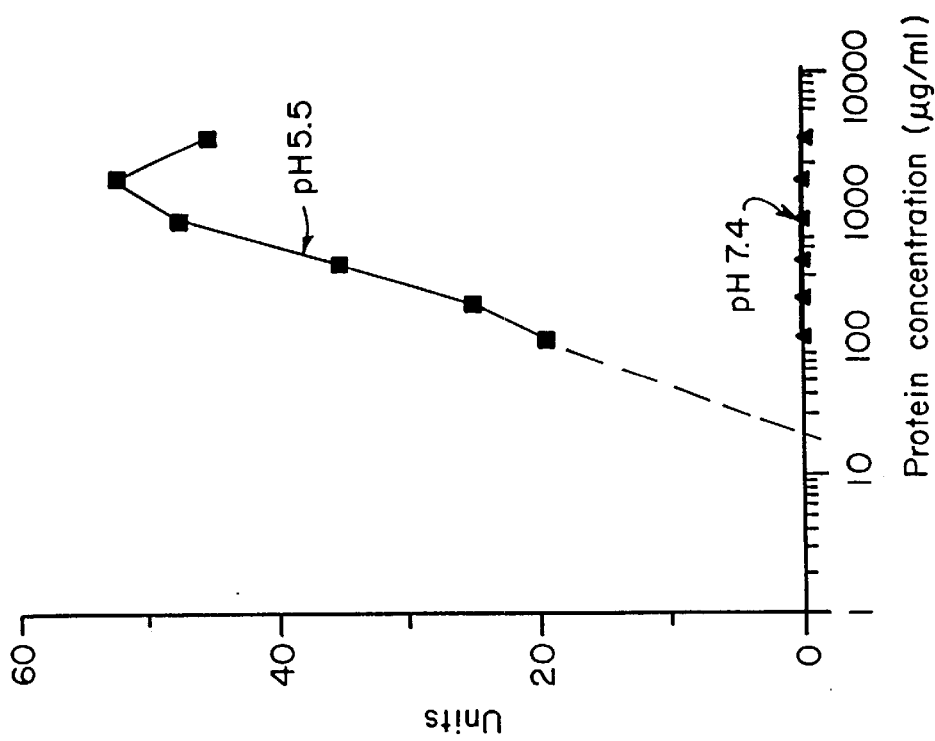
FIG. 8: Activity of alpha chain against *Escherichia coli* at pH 5.5 and pH 7.4.
Figure 7:
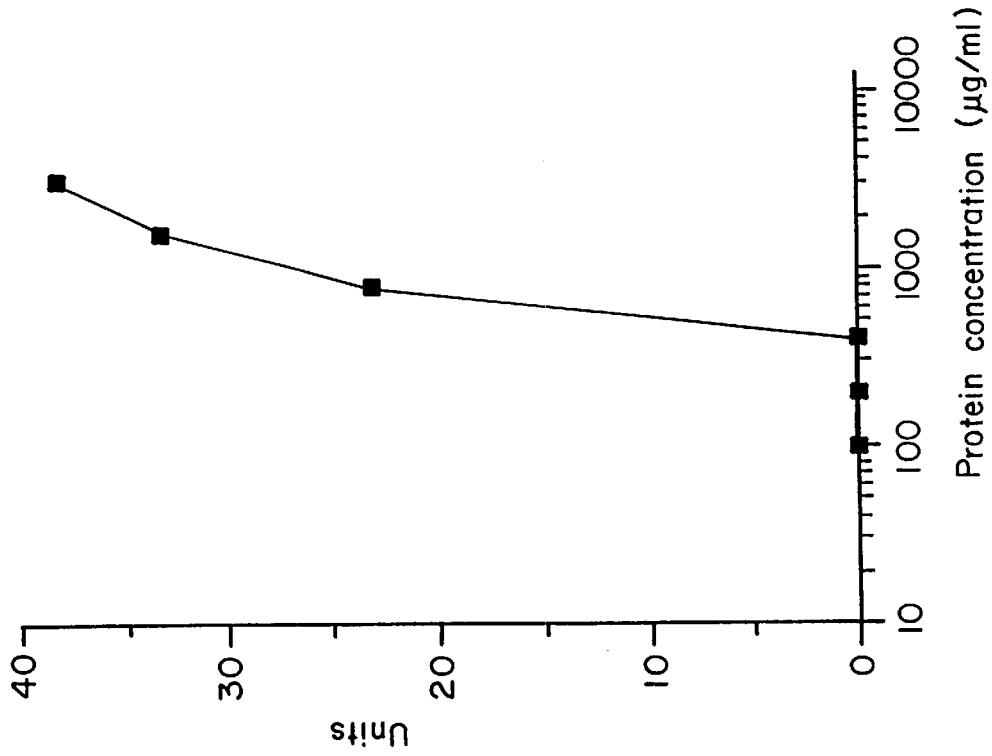
FIG. 7: Activity of alpha chain against *Candida albicans* at pH 5.5.
Figure 10:
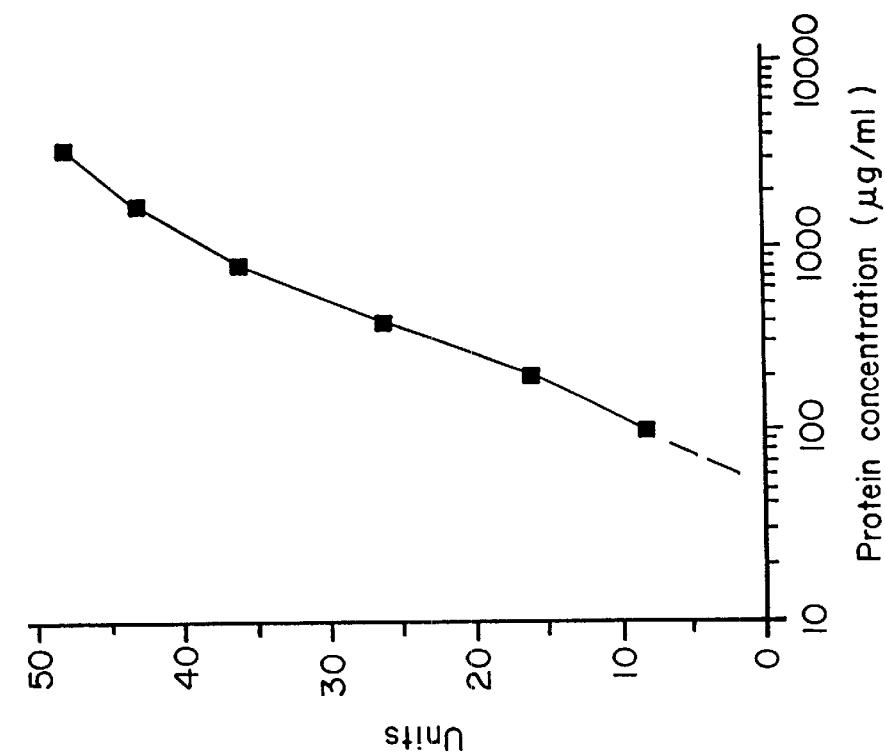
FIG. 10: Activity of alpha chain against *Pseudomonas aeruginosa* at pH 5.5.
Figure 9:
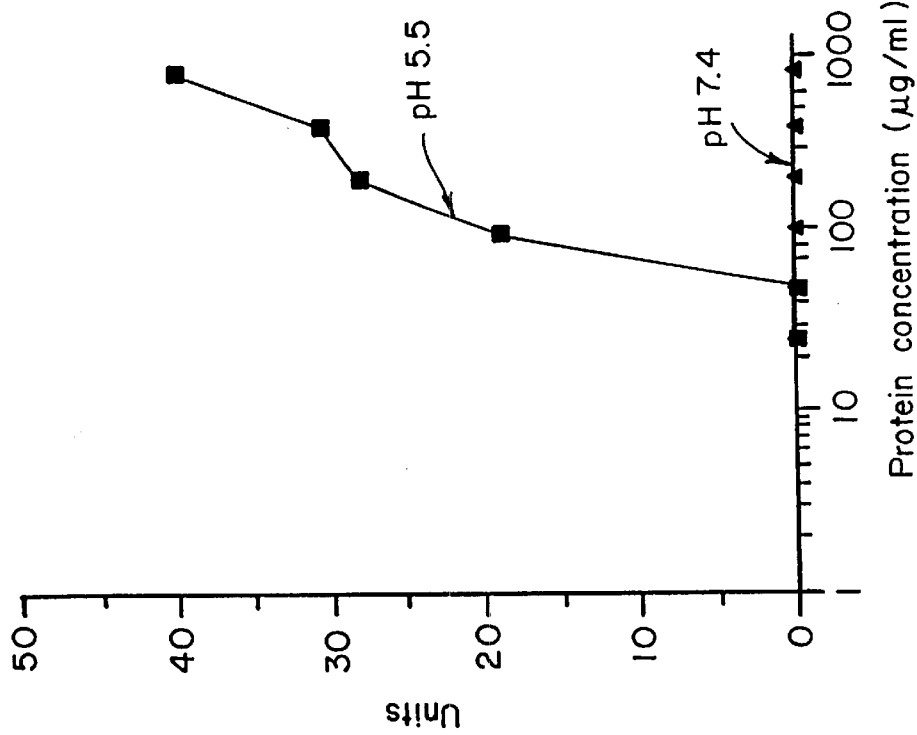
FIG. 9: Activity of alpha chain against *Escherichia coli* at pH 5.5 and pH 7.4.
Figure 14:
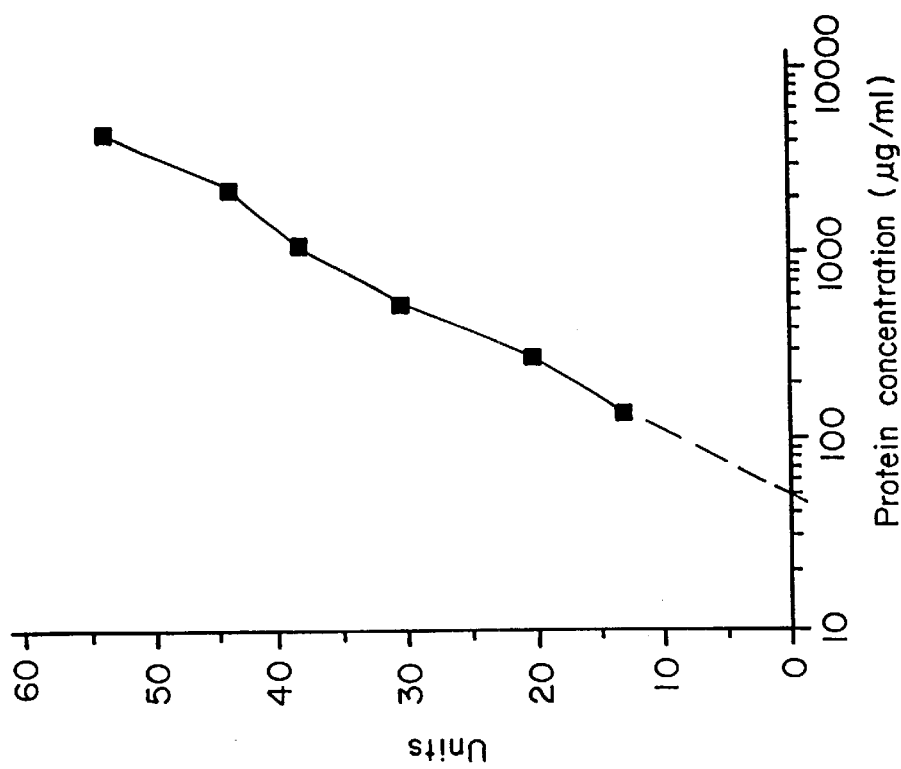
FIG. 14: Activity of beta chain against *Candida albicans* at pH 5.5.
Figure 13:
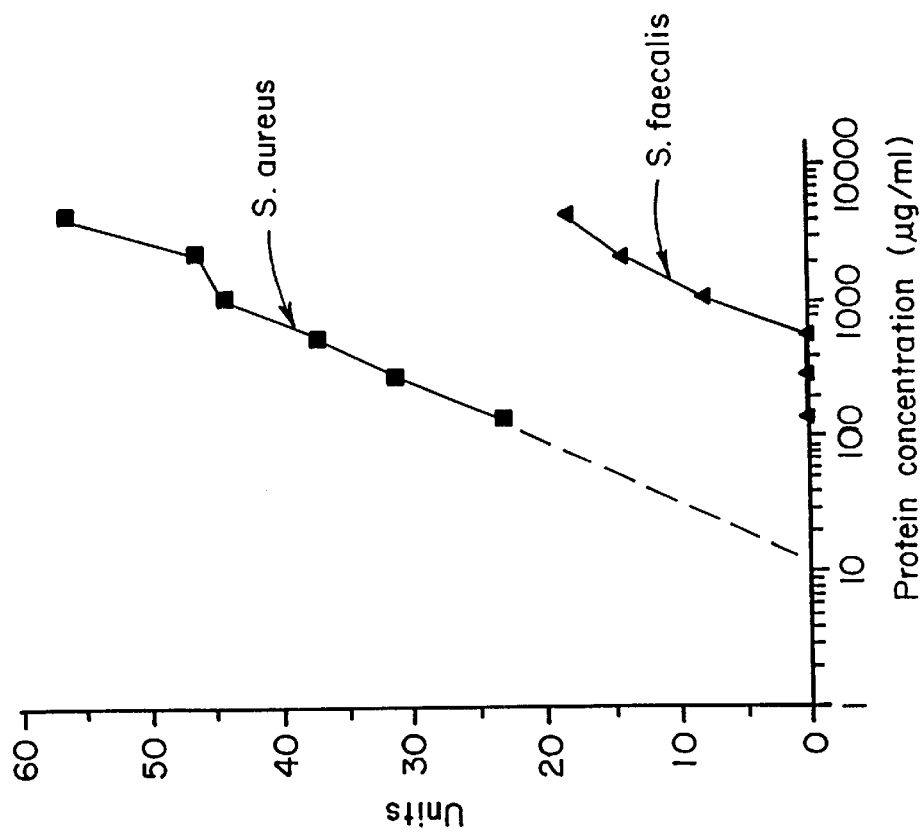
FIG. 13: Activity of beta chain against *Staphylococcus aureus* and *Streptococcus faecalis* at pH 5.5.
Figure 15:
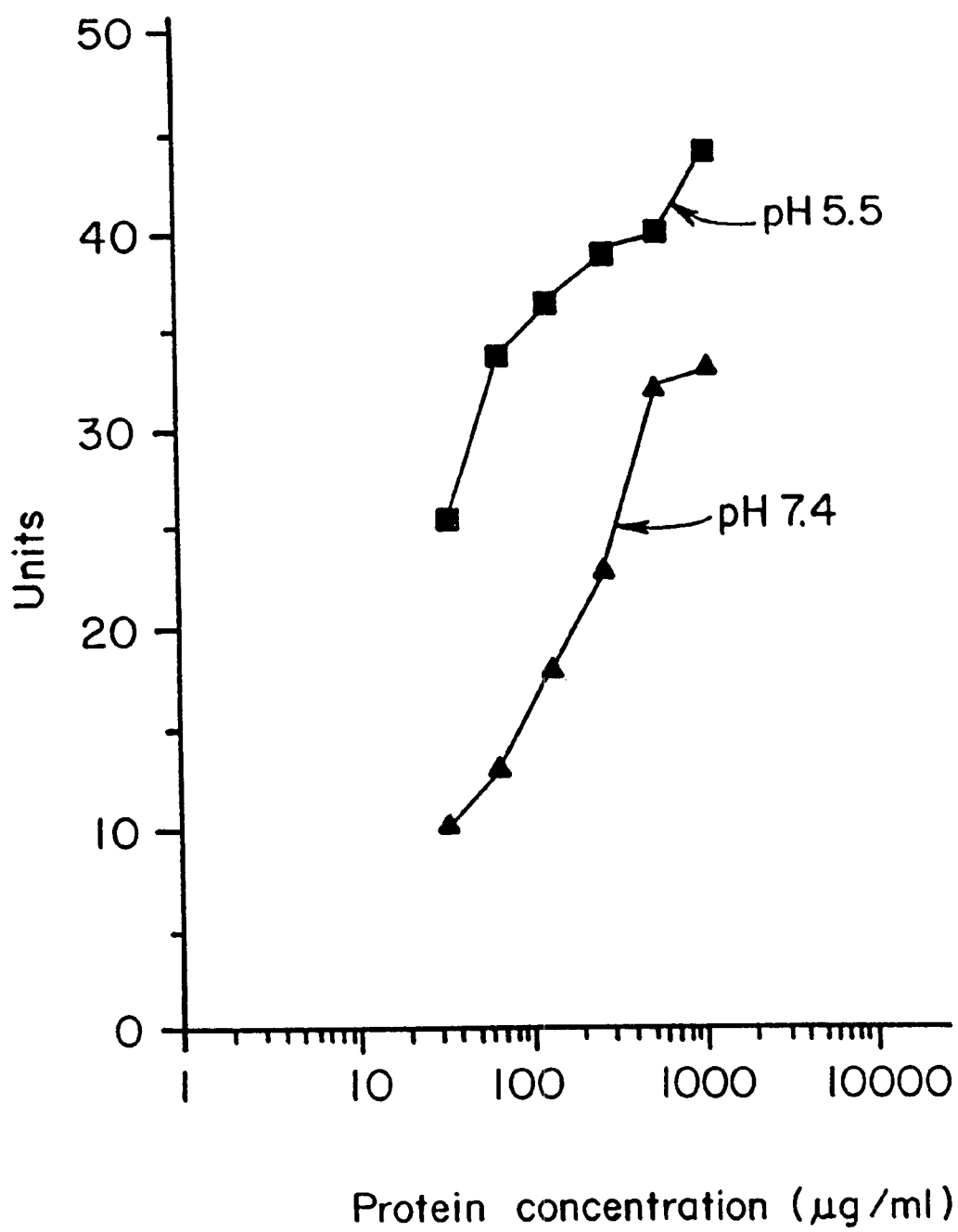
FIG. 15: Activity of beta chain against *Escherichia coli* at pH 5.5 and pH 7.4.

The subject of the invention is the antimicrobial activity of mammalian hemoglobin, its heme-free α and β chains, selected fragments thereof, synthetic peptides therefrom and compositions comprising such peptides and fragments. Therapeutic applications for these substances include use as broad spectrum topical and systemic antibacterial and antifungal agents, and agents exhibiting synergism with standard antibiotics.

This invention further provides compositions of matter and methods for treating microbial infections. More particularly, the compositions of this invention comprise hemoglobin or its α or β chains, the latter without heme, derived from human red blood cells or red blood cells of mammals.

Further, these compositions also include polypeptide fragments of the α and β chains of hemoglobin that result from cleavage of the α or β chain with cyanogen bromide (CNBr) or other peptidases and synthetic peptides therefrom. Bacteria against which the compositions have bactericidal activity include Gram negative bacteria. Examples of such Gram negative bacteria are *Escherichia coli* and *Pseudomonas aeruginosa*. The compositions are also active against Gram positive bacteria. Examples of such Gram positive bacteria are *Staphylococcus aureus* and *Streptococcus faecalis*. Additionally, the compositions act as antimicrobial agents against fungi including yeast. In one embodiment of the invention, the yeast is *Candida albicans*.

Human hemoglobin exerts antimicrobial activity against fungi, such as *Candida albicans*, Gram-negative bacteria, such as *Escherichia coli* and *Pseudomonas aeruginosa* and Gram-positive bacteria such as *Staphylococcus aureus* and *Streptococcus faecalis*. (FIGS. 1 to 6) Antimicrobial activity is effected by pH, being greater at pH 5.5 than at pH 7.4.

Similar antimicrobial activity is exhibited for the heme-free α and β chains of hemoglobin. (FIGS. 7 to 10 for heme-free α chain; and FIGS. 11 to 15 for the heme-free β chain.) As with intact hemoglobin, antimicrobial activity for the heme-free α and β chains of hemoglobin is effected by pH, being greater at pH 5.5 than at pH 7.4.

Further, antimicrobial activity is demonstrated by fragments of the α and β chains that result when either hemoglobin or the individual α and β chains are cleaved by CNBr.

CNBr treatment results in three fragments for the α chain and two fragments for the β chain.

```
α-1                                              (SEQ ID NO:7)
1             15    16            30  31
VLSPADKTNVKAAWG     KVGAHAGEYGAEALE   RM

α-2                                              (SEQ ID NO:8)
33            45    46            60  61            75
FLSFPTTTKTYFPH      FDLSHGSAQVKGHGK    KVADALTNAVAHVDD
76
M

α-3                                              (SEQ ID NO:3)
77            90    91           105  106          120
PNALSALSDLHAHK      LRVDPVNFKLLSHCL    LVTLAAHLPAEFTPA
121          135    136
VHASLDKFLASVSTV     LTSKYR

β-1                                              (SEQ ID NO:9)
1             15    16            30  31            45
VHLTPEEKSAVTALW     GKVNVDEVGGAELGR    LLVVYPWTQRFFESF
46            55
GDLSTPDAVM

β-2                                              (SEQ ID NO:2)
56  60              61            75  76            90
GNPKV               KAHGKKVLGAFSDGL    AHLDNLKGTFATLSE
91           105    106          120  121          135
LHCDKLHVDPENFRL     LGNVLVCVLAHHFGK    EFTPPVQAAYQKVVA
136          146
GVANALAHKYH
```

The α-3 cleavage fragment is identified as:

```
1                                                (SEQ ID NO:3)
PNALSALSDLHAHKLRVDPV
21
NFKLLSHCLLVTLAAHLPAEF
41                    64
TPAVHASLDKFLASVSTVLTSKYR
``` and
the following fragment is identitied as:
```
1                                                (SEQ ID NO:4)
KAHGKKVLGAFSDGLAHLDN
21
LKGTFATLSELHCDKLHVDP
41
ENFRLLGNVLVCVLAHHFGK
61
EFTPPVQAAYQKVVAGVANA
```

```
81    86
LAHKYH
```

The discovery of antimicrobial activities of human hemoglobin and its two subunits prompted the examination of the minimal requirements for biological activity so as to design model compounds with similar activity. As discussed above, the cleavage with CNBr yielded 5 fragments: 3 from α chain and 2 from β chain. Fragment β2 was highly active against *E. coli* and *C. albicans*. The-tertiary structure of β2 indicates that both ends of this fragment are helices. Two peptides derived from the ends of β2 were synthesized and tested for antibiotic activity.

Peptide I: GNPKVKAHGKKVLGAFS (SEQ ID NO: 5)
Peptide II: HHFGKEFTPPVQAAYQKVVAG-VANALAHKYH (SEQ ID NO: 6)

Each of the synthetic peptides shows antimicrobial activities.
(See Table 3, Examples 9 and 10.)

Although any mechanism proposed to account for the action of these peptides should not be considered limiting, it may be that the antimicrobial activity is contributed from the helix structure of the peptides which may form pores inside the membrane of the microorganisms. Because of similarities in the structure and configuration of hemoglobins from a variety of mammals, it is likely that hemoglobin, its α and β chains and fragments thereof obtained from sources other than human will exert significant antimicrobial activity. The invention thus also encompasses hemoglobin tetramers and their constituent heme-free monomers from other mammals.

The compositions of the invention may be used therapeutically, as preservatives or as disinfectants. This invention thus comprises a method for antimicrobially treating bacteria or fungi. This method comprises exposing the bacteria or fungi to an antimicrobially effective amount of one of the compositions described herein according to any and each of the technologies described herein. When carrying out the method, the compositions are typically dissolved in an appropriate buffer. Examples of appropriate buffers are known in the art and include phosphate buffer (for fungi) or phosphate buffered saline at suitable values of pH.

The invention further provides a pharmaceutical composition useful for treating bacterial or fungal infections in a human or other mammalian subject by-topical or systemic application. This pharmaceutical composition comprises an antimicrobially effective amount of one of the compositions of the invention and a pharmaceutically acceptable carrier. Suitable pharmaceutically acceptable carriers for topical, oral or systemic use are known in the art and are disclosed in the Pharmacopeia of the United States, The National Formulary and Pharmaceutical Science ($8^{th}$ Edition, Chapters 83, 84 and 89).

Depending on the specific application contemplated, the pharmaceutical composition provided by the present invention may be formulated as a solution, suspension, parenteral preparation, ointment, cream, lotion, spray, powder, tablet or capsule which is dosed, applied or admixed as appropriate. Parenteral preparations may include a vehicle such as specially distilled pyrogen-free water, phosphate buffer, or normal saline. Ointments, creams, lotions and sprays may include a carrier such as vegetable or mineral oil, white petrolatum, or a high molecular weight alcohol, i.e., possessing greater than 12 carbon atoms. Tablets or capsules may include diluents, e.g., lactose, binders, lubricants, e.g., stearic acid, and a disintegration aid, e.g., corn starch.

Each of the compositions of this invention may be combined with other antibiotics or antimicrobial agents, antiprotozoal agents, wound-healing agents and the like to enhance their activity or therapeutic spectrum.

Also provided is a method for treating a human or other mammalian subject having a bacterial or fungal infection which comprises administering to the subject an antimicrobially effective amount of one of the pharmaceutical compositions of the present invention. The compositions can be administered to the subject by, for example, intravenous injection, intraperitoneal injection, orally, or in the form of an aerosol spray composition. Lipid vesicles or lipid emulsion preparations containing the peptides of the invention can also be used for administering the compositions. Specific modes of administration will depend on the pathogen to be targeted. The selection of the specific route of administration and the dose regimen is to be adjusted or titrated by the clinician according to methods known to said clinician in order to obtain the optimal clinical response. The amount to be administered is that amount which is antimicrobially effective. The dosage administered will also depend on the characteristics of the subject being treated, e.g., the particular mammal treated, age, weight, health, types of concurrent treatment, if any, frequency of treatments, and therapeutic ratio. In the case of the treatment of human subjects, the antimicrobially effective amount will typically be in the range of from about 0.5 to 50 mg/kg body weight, and in the range of from about 0.5–5.0 mg/ml per dose.

Also provided is a method for using such peptides to prevent microbial contamination of food, i.e. as a preservative or to eliminate potential pathogens. For example, shell fish, meats and poultry products routinely habor the growth of enteric pathogens. Such pathogens can be eliminated by treatment with an antimocrobially effective amount of the peptide compositions of the invention. Food crops, such as fruits and vegetables could also be treated to eliminate post harvest spoilage. The peptides could be administered topically or through transgenic expression of a recombinant peptide of the invention. In the instance where the material to be preserved is mixed with the composition of the invention, an antimicrobially effective amount of the selected peptide is added by a simple blending method. The antimicrobially effective amount will typically be in the range of from about 1500 $\mu$g to 50 mg/kg of treated material. In the instance where the compositions are administered topically, the antimicrobially effective amount will typically be in the range of from about 0.1–1.0 mg/cm$^2$.

Additionally, the peptides of the invention can be used as disinfectant agents to sterilize or maintain microbe-free products. Such products can include baby wipes, diapers, bandages, towelettes, make-up products, eyewash and contact lens solutions. The compositions of the invention may be administered to such products topically, in appropriate buffer or in liposome compositions. The antimicrobially effective amount to be administered will typically be in the range of from about about 1500 $\mu$g to 50 mg/kg of treated material.

The following examples are intended to illustrate but not limit the present invention.

EXAMPLES

METHODS AND PREPARATIONS
Separation of $\alpha$ and $\beta$ Chains from Hemoglobin (30,31).

Figure 16:
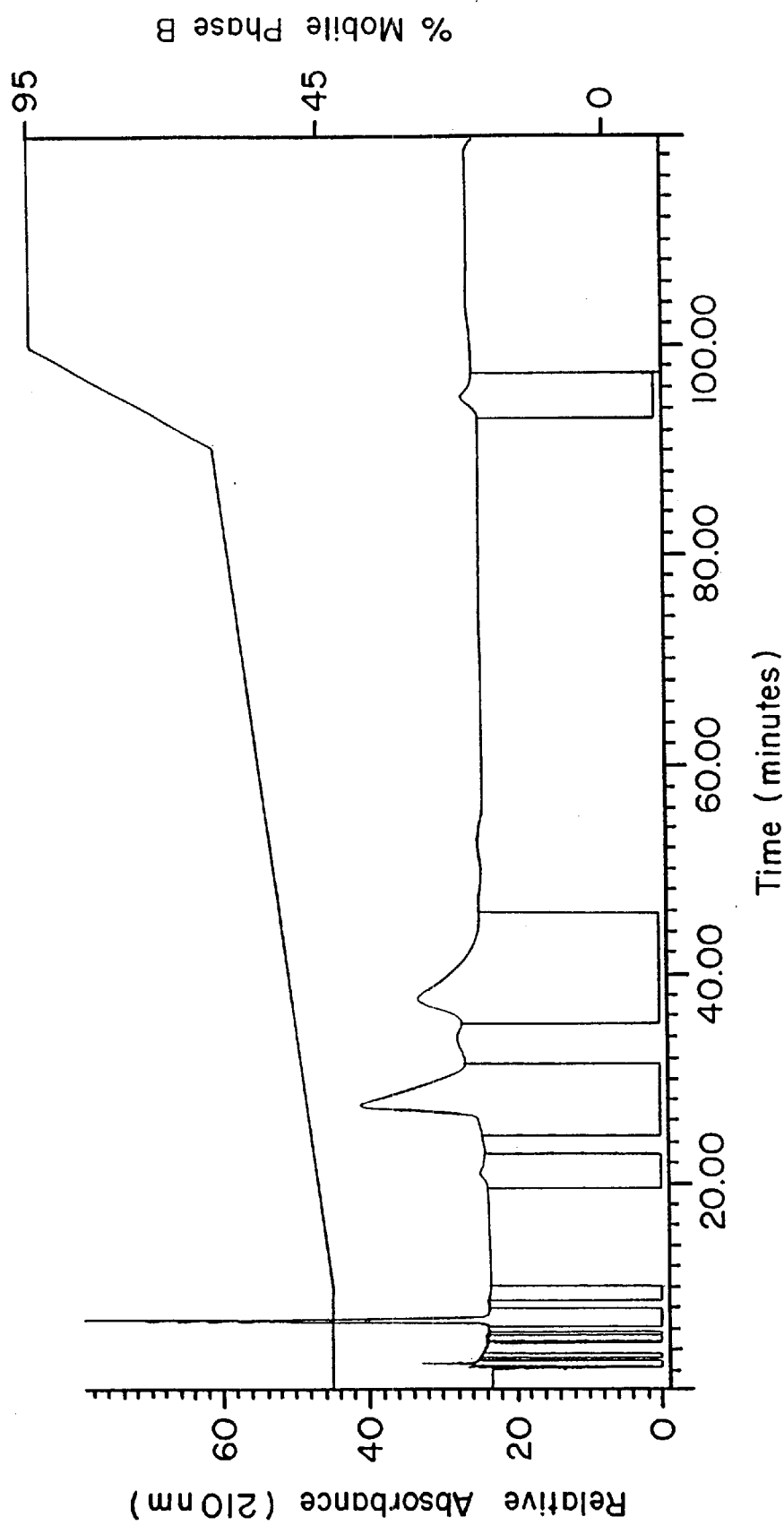
FIG. 16: Plot of C4-reverse phase HPLC analysis of human hemoglobin chains showing an early peak representing heme and subsequent broader peaks representing the beta and alpha chains respectively.

Crude Hb (50 $\mu$L), purchased from Sigma Chemicals, was injected onto a C4 reverse-phase HPLC column (YMC Protein-RP, 150×4.6 mm I.D.) and eluted with water/acetonitrile (mobile phase A; 80% H$_2$O/20% AcCN/0.1 TFA; mobile phase B: 40% H$_2$O/60% AcCN/0.1 TFA). The column was initially washed with 40% mobile phase B for 10 min, after which a linear gradient was run from 45% to 60% of B over 90 min. A second linear gradient from 55% to 95% of B was run over 10 min, after which the column was maintained at 95% B for 15 min. The flow rate of the column was 1 mL/min and eluted material was detected at 210 nm. The eluted volume was collected in 4 mL fractions which were concentrated under vacuum. The heme eluted as a sharp peak at 7.15 min, while the $\beta$ and $\alpha$ subunits eluted as broad peaks centered at 28 min and 38 min, respectively (FIG. 16).

Tris/Tricine-SDS-PAGE Analysis of Hemoglobin and its $\alpha$ and $\beta$ Chains (32).

Figure 17:
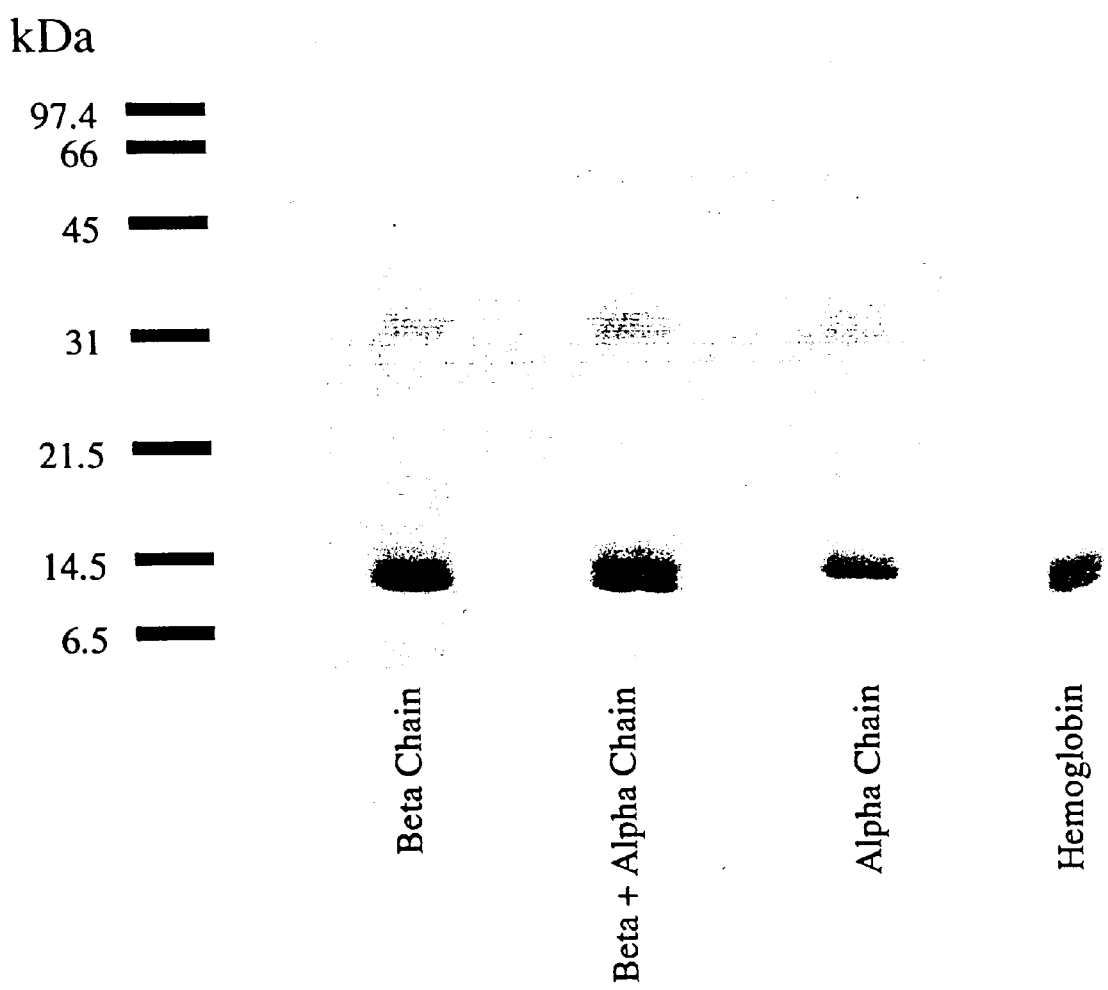
FIG. 17: Tris-tricine-SDS-PAGE analysis of human hemoglobin showing coomassie blue staining of both the alpha and beta chains at 14.5 kDa.

Aliquots (20 $\mu$L) of Hb and its $\alpha$ and $\beta$ chains were combined with 6× sample buffer (4 $\mu$L), heated at 95° C. for 5 min and analyzed by SDS-PAGE (16.5% gel) using a tris/tricine buffer system. The bands were visualized by coomassie blue staining (0.1% coomassie blue G-250 in 50% methanol/10% acetic acid) for 1 %, followed by destaining of each gel (5% methanol/7% acetic acid) overnight (FIG. 17).

Cyanogen Bromide (CNBr) Cleavage of Human $\alpha$ and $\beta$ Hemoglobin Chains Human $\alpha$ and $\beta$ chains were diluted with formic acid (60% final formic acid concentration). Then cyanogen bromide (500–1,000 fold excess) was added as a solution of AcCN (4.7 M). Each reaction was flushed with argon and placed in the dark at room temperature for 24 hours. Since the cleavage procedure employed HCOOH, any resulting fragments would likely be formulated, a result that would yield multiple peaks for each fragment of HPLC analysis. To overcome this problem ethanolamine (100 $\mu$L of ethanolamine per 1 mg. starting material) was added to the samples which then were vortexed, sonicated and again dried in vacuo. Materials were redissolved with sonication in 10 mM sodium phosphate buffer (NaPB) at pH 5.5.

Figure 18A:
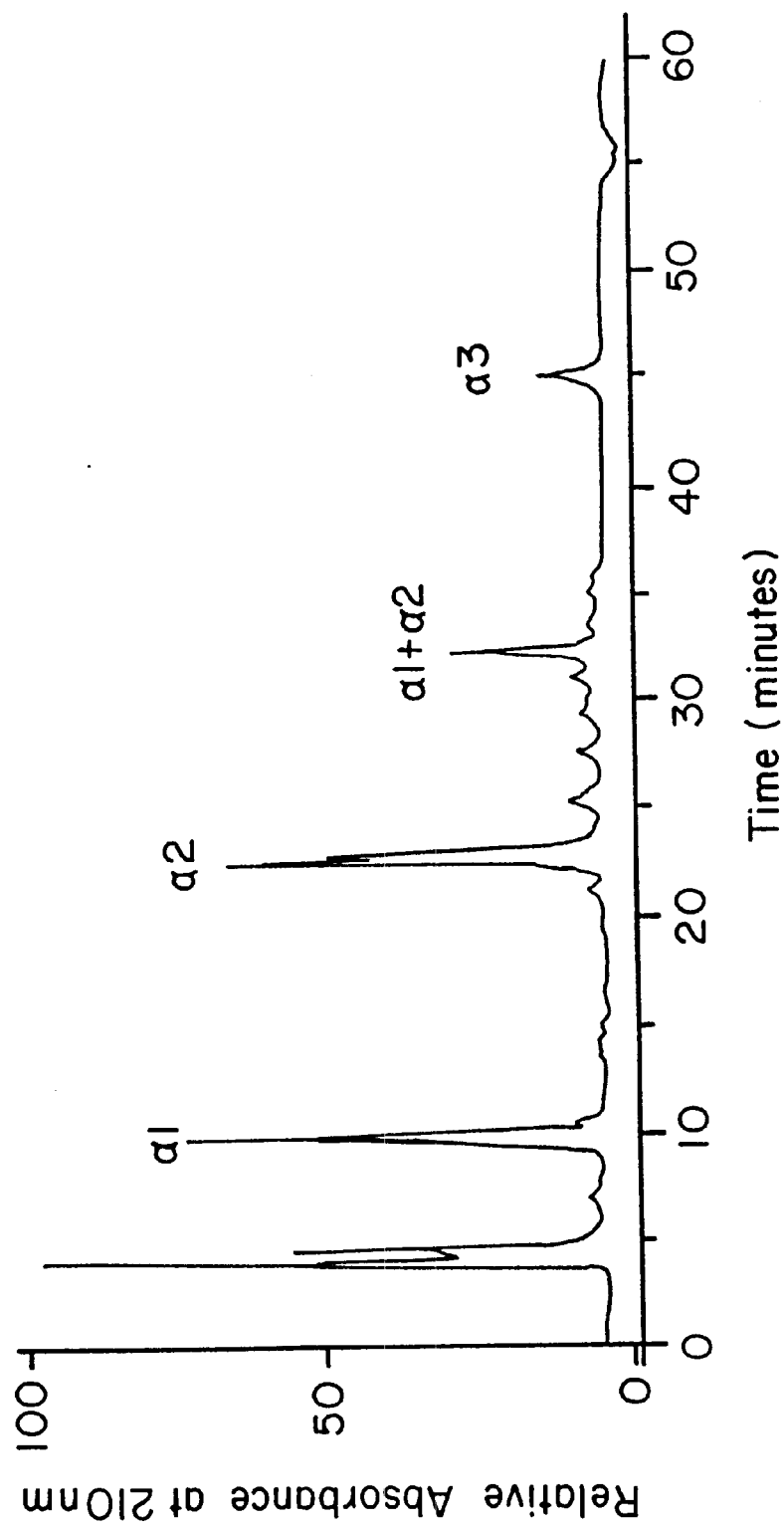
FIG. 18A: HPLC Separation of CNBr-cleaved fragments of human hemoglobin α chain.
Figure 18B:
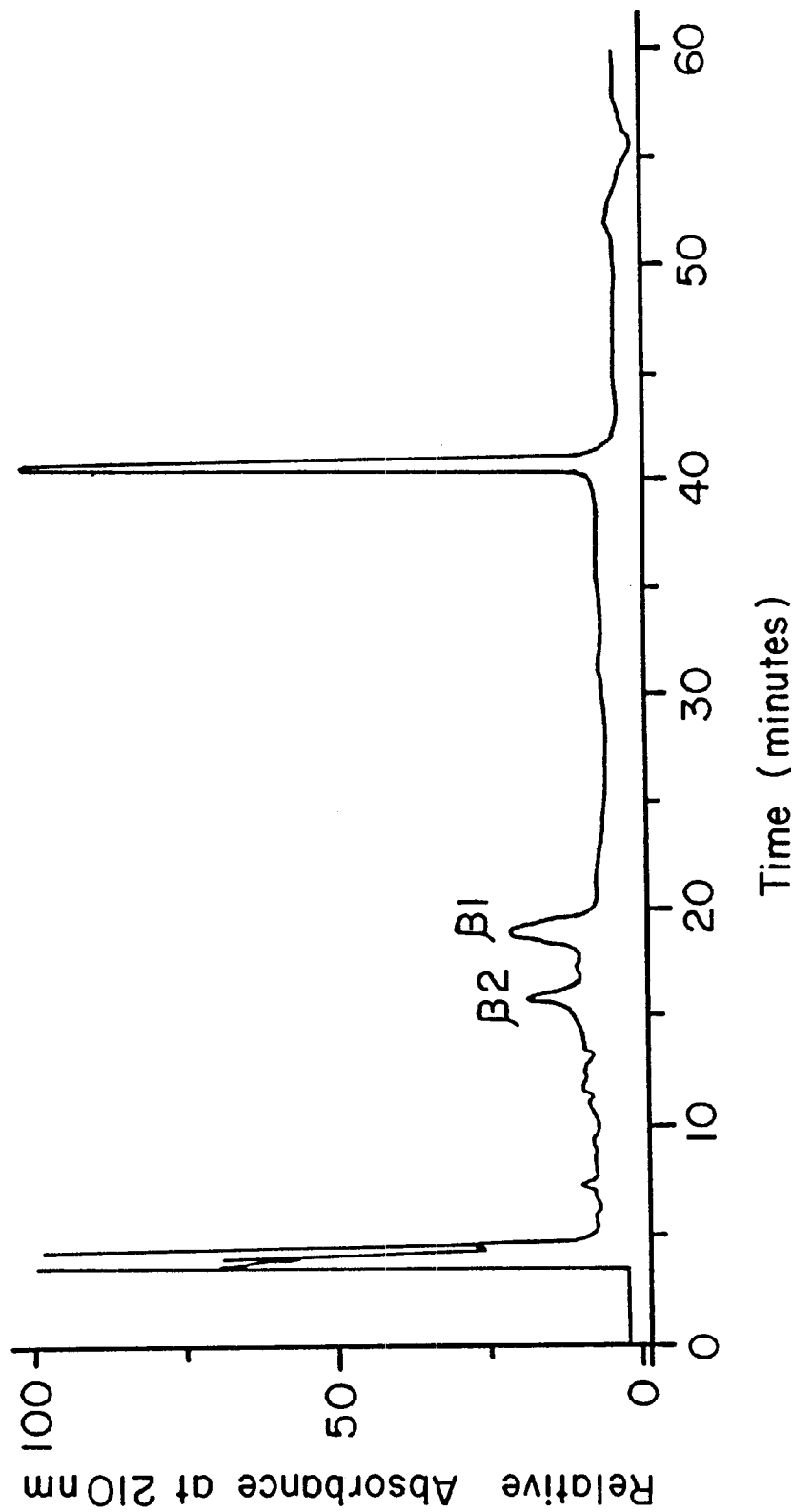
FIG. 18B: HPLC Separation of CNBr-cleaved fragments of human hemoglobin β chain.
Figure 19A:
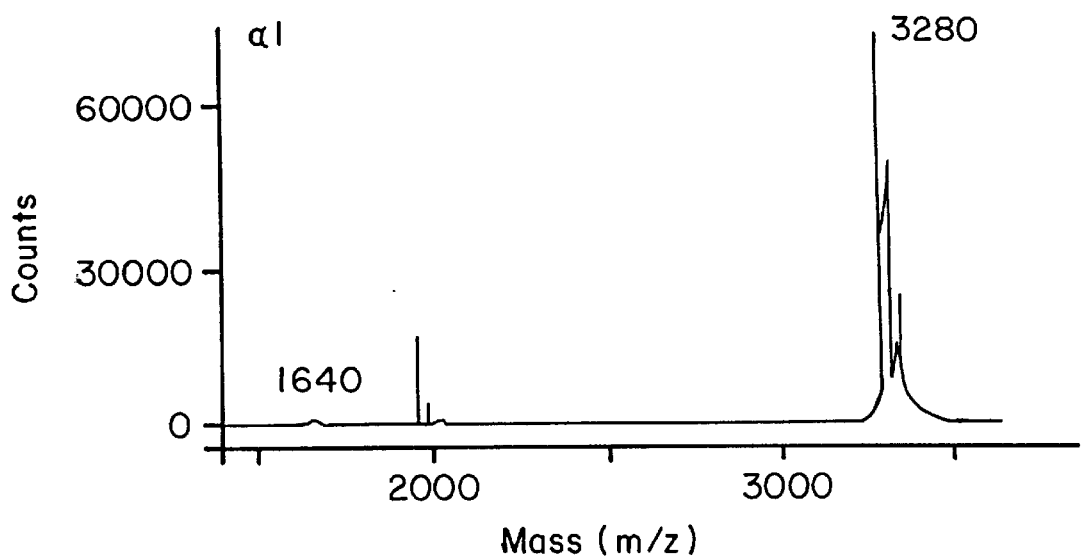
FIG. 19A: MALDI-TOF mass spectroscopic analysis of CNBr-cleaved α1 fragment of human hemoglobin αchain.
Figure 19B:
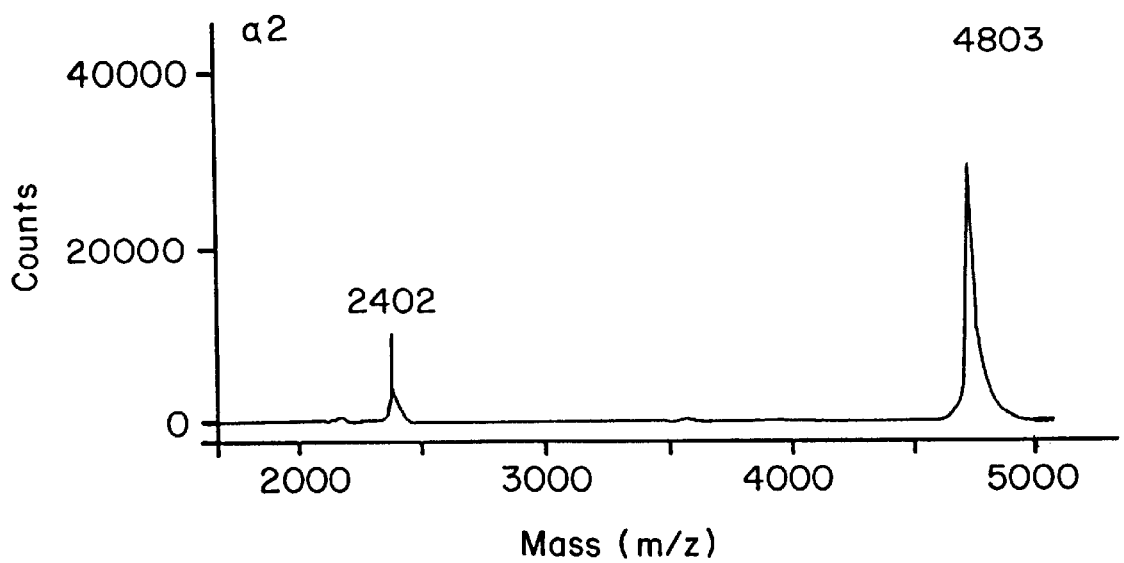
FIG. 19B: MALDI-TOF mass spectroscopic analysis of CNBr-cleaved α2 fragment of human hemoglobin α chain.
Figure 19C:
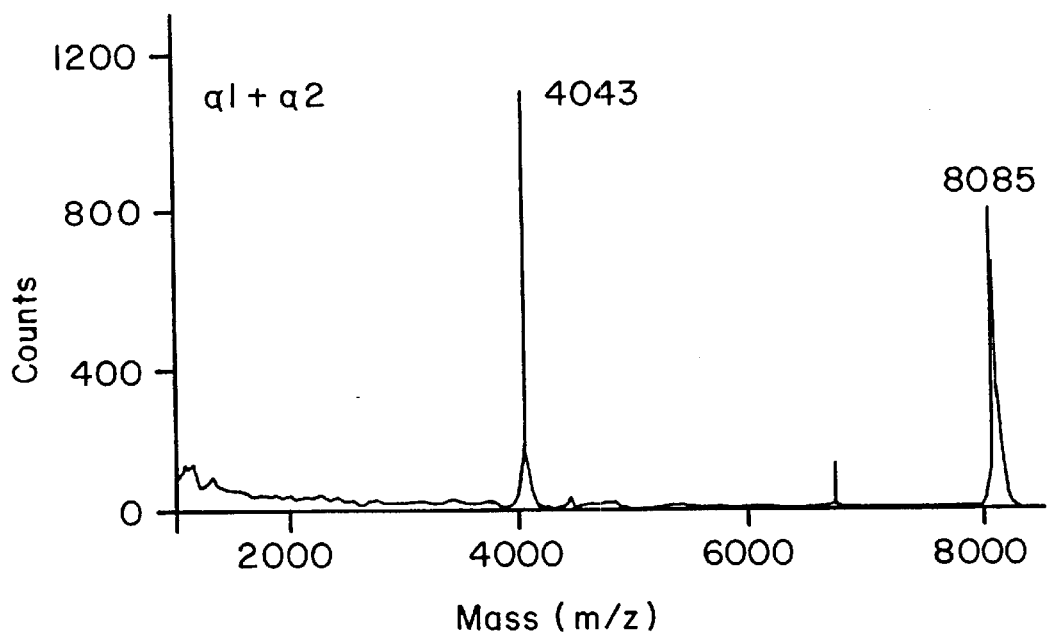
FIG. 19C: MALDI-TOF mass spectroscopic analysis of CNBr-cleaved α1 and α2 fragments of human hemoglobin a chain.
Figure 19D:
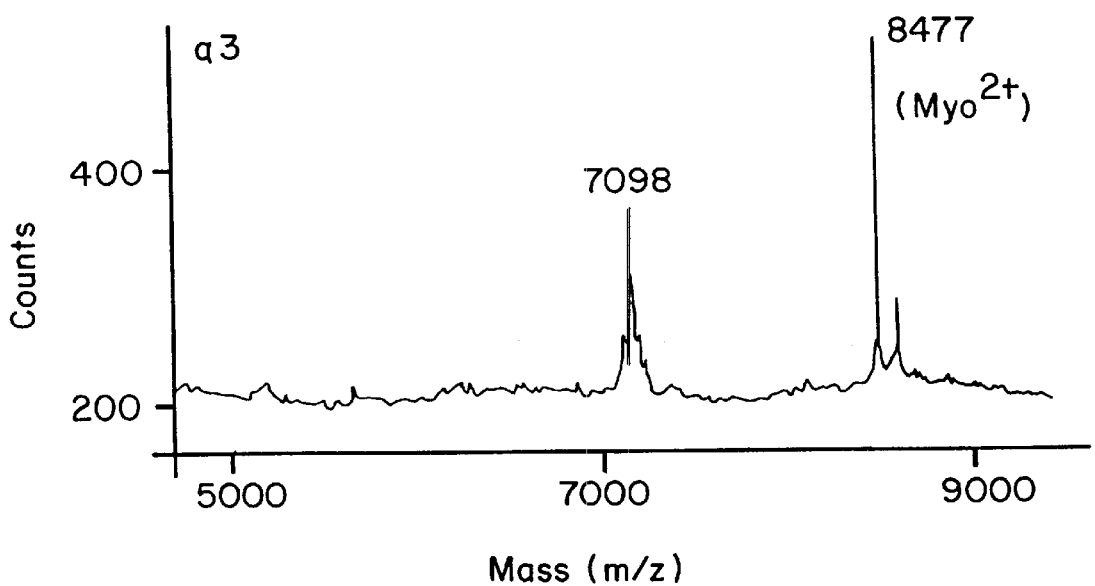
FIG. 19D: MALDI-TOF mass spectroscopic analysis of CNBr-cleaved α3 fragment of human hemoglobin αchain.
Figure 19E:
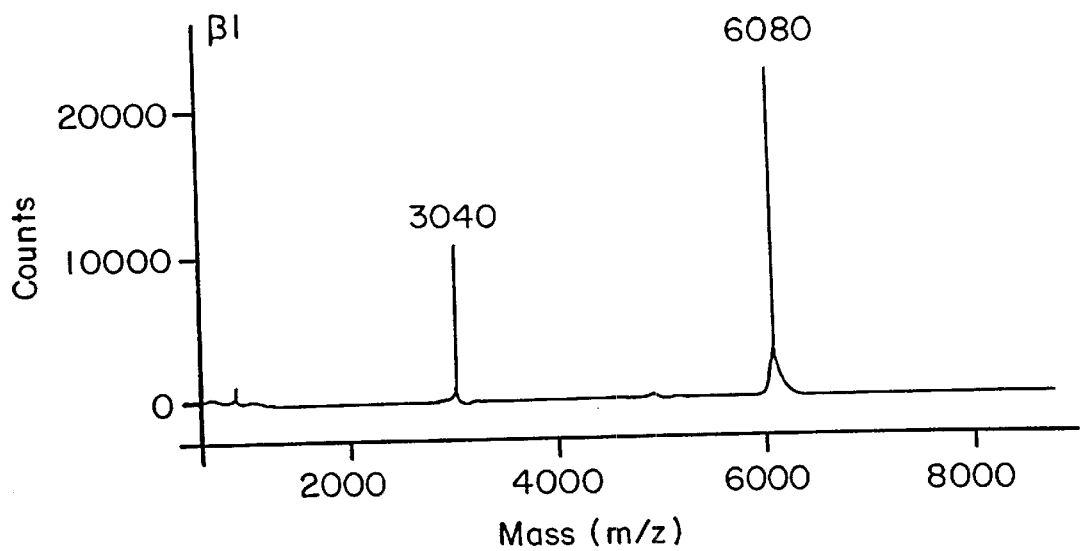
FIG. 19E: MALDI-TOF mass spectroscopic analysis of CNBr-cleaved β1 fragment of human hemoglobin β chain.
Figure 19F:
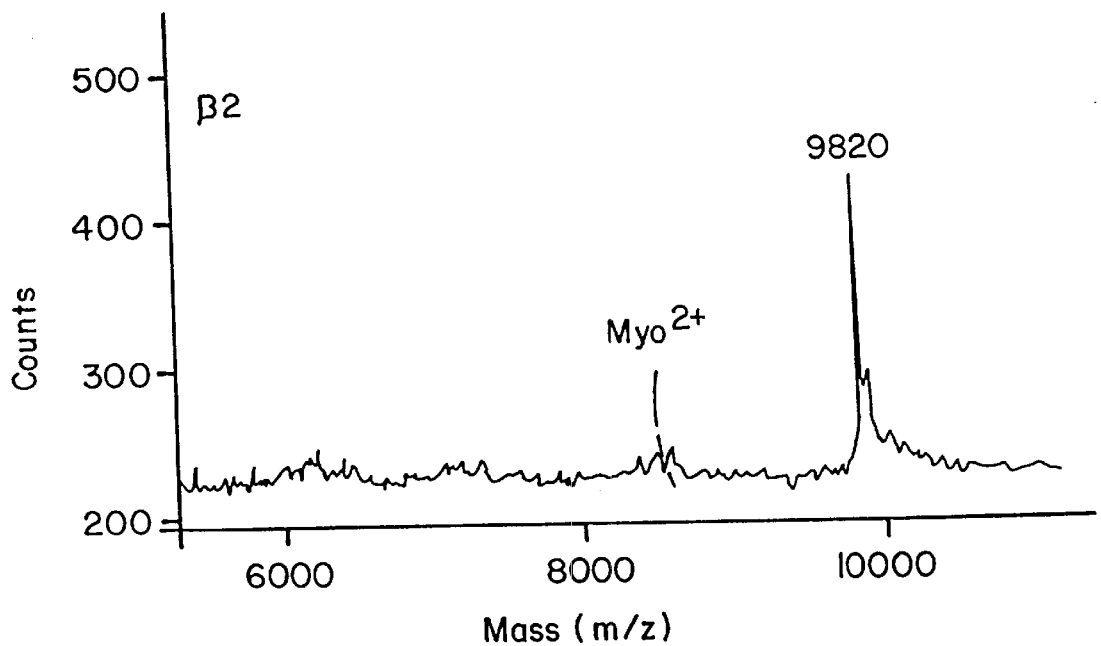
FIG. 19F: MALDI-TOF mass spectroscopic analysis of CNBr-cleaved β1 fragment of human hemoglobin β chain.

Reversed phase HPLC was used to separate the peptide fragments (FIG. 18, A&B).

The theoretical cleavage pattern of human hemoglobin $\alpha$ and $\beta$ chains is expected to yield, for the $\alpha$ chain, three peptides containing 32,44 and 65 amino acids and, for the $\beta$ chain, two peptides containing 55 and 91 amino acids. MALDI-TOF mass spectroscopic analysis of the CNBr-cleaved fragments of the $\alpha$ and $\beta$ chains is shown in FIG. 19, A–F.

Measurement of Antimicrobial Activity

Microbes utilized in the described assays were as follows: *Staphylococcus aureus* was strain RN6390, *Pseudomonas aeruginosa* was strain PA01, *Escherichia coli* was strain MC4100, *Streptococcus faecalis* was ATCC 8043 and *Candida albicans* was a clinical isolate from the Presbyterian Hospital.

Antibacterial Activity

A. Plate assay

The antibacterial activity of purified fractions, hemoglobin or its $\alpha$ and $\beta$ chains, or the CNBr derived fragments of those chains were tested against bacteria, typified by *Escherichia coli*, maintained on Trypicase Soy Broth (TSB) agar plates. *Escherichia coli* is used as a representative of Gram-negative organisms. A single colony is inoculated into trypticase soy broth and grown to mid-exponential phase (OD$_{600}$=0.75). The cultures are washed and diluted in NaPB (pH 5.5 or 7.4), 150 mM NaCl (PBS) to a final concentration of 2×10$^4$ colony forming units (CFU)/ml. Bacteria are incubated for 1 hour at 37° C. with suitable concentrations of hemoglobin or the $\alpha$ or $\beta$ chains in PBS assay buffer. At the end of the assay, aliquots are diluted 1:10 in PBS and plated on agar plates with 0.8% soft agar to determine bacterial survival after overnight incubation at 37° C. Bactericidal activity is determined by calculating the decrease in colony forming units for bacteria incubated with hemoglobin or its α or β chains as compared to bacteria incubated with buffer alone.

B. Radial diffusion assay for antibiotic activity against *Staphylococcus aureus* RN6390

A single colony of *Staphylococcus aureus* RN6390 is inoculated into CYGP broth and grown to mid-exponential phase ($OD_{600}$=0.7). The cultures are washed in NaPB pH 5.5 and dissolved to a final concentration of $5 \times 10^7$ CFU/ml. A 0.2 ml aliquot of this bacterial suspension ($10^7$ CFU) is added to 10 ml of autoclaved and cooled (to 42° C.) NaPB buffer, 1% w/v of low electroendosmosis type agarose (Sigma). After mixing the bacteria in, the agarose is poured in Lab-Tek square Petri dishes to form a uniform thick layer. Wells with a 2.7 mm diameter are punched in and filled with 4.5 ul of control or sample, the plates are incubated for 3 hours at 37° C., and overlaid with 10 ml of sterile agar maintained at 42° C. The overlay agar is 2× CYGP broth and 1% w/v Bacto-agar. After incubation for 18–24 hours at 37° C., the diameter of the clear zone surrounding the wells containing an antibacterial agent is measured.

C. Radial diffusion assay for antibiotic activity against *Pseudomonas aeroginosa* PA01

A single colony of *Pseudomonas aeroginosa* PA01 is inoculated into trypticase soy broth and grown to mid-exponential phase ($OD_{600}$–0.7). The cultures are washed in NaPB pH 5.5 and dissolved to a final concentration of $5 \times 10^7$CFU/ml. A 0.2 ml aliquot of this bacterial suspension ($10^7$CFU/ml) is added to 10 ml of autoclaved and cooled (to 42° C.) NaPB buffer, 1% w/v of low electroendosmosis type agarose (Sigma). After mixing the bacteria in, the agarose is poured in Lab-Tek square Petri dishes to form a uniform thick layer. Wells with a 2.7 mm diameter are punched in and filled with 4.5 ul of control or sample, the plates are incubated for 3 hours at 37° C., and overlaid with 10 ml of sterile agar maintained at 42° C. The overlay agar is 6% (w/v) TSB and 1% w/v Bacto-agar. After incubation for 18–24 hours at 37° C., the diameter of the clear zone surrounding the wells containing an antibacterial agent is measured.

D. Radial diffusion assay for antibiotic activity against *Escherichia coli* MC4100

A single colony of *Escherichia coli* MC4100 is inoculated into trypicase soy broth and grown to mid-exponential phase ($OD_{600}$–0.7). The cultures are washed in NaPB pH 5.5 and dissolved to a final concentration of $5 \times 10^7$CFU/ml. A 0.2 ml aliquot of this bacterial suspension ($10^7$CFU/ml) is added to 10 ml of autoclaved and cooled (to 42° C.) NaPB containing 0.02% Bovine Serum Albumin (BSA) and 0.02% Triton X100., 1% w/v of low electroendosmosis type agarose (Sigma). After mixing the bacteria in, the agarose is poured into Lab-Tek square Petri dishes to form a uniform thick layer. Wells with a 2.7 mm diameter are punched in and filled with 4.5 ul of control or sample, the plates are incubated for 3 hours at 37° C., and overlaid with 10 ml of sterile agar maintained at 42° C. The overlay agar is 6% (w/v) TSB and 1% w/v Bacto-agar. After incubation for 18–24 hours at 37° C., the diameter of the clear zone surrounding the wells containing an antibacterial agent is measured.

E. Radial diffusion assay for antibiotic activity against *Streptococcus faecalis* ATCC 8043

A single colony is inoculated in 10 mL of TSB overnight shaking at 37C. Approximately 0.3 ml is added to 10 mL fresh TSB and shaken at 37° C. This is allowed to grow to mid-log phase ($OD_{600}$=0.6). The culture is washed 2× in NaPB pH 5.5 by spinning at 5000 rpm. for 10 min. OD is rechecked after washing to determine exact bacterial concentration. The washed bacteria are added at a concentration of $10^7$/plate to the lower layer (NaPB pH 5.5/1% Low Electroendosmosis agarose). Dilutions of Hemoglobin dilutions in NaPB pH 5.5 are added to the plate, allowed to diffuse in the layer, and incubated in wet box at 37C for 3 hours. Following the incubation, 10 mL of nutrient medium, 6% TSB and 1% Bactoagar, is added as a top layer and plates are incubated in the wet box overnight at 37±C.

Antifungal Activity

A. Plate assay

The antifungal activity of hemoglobin or its α or β chains is tested against a fungus, as typified by *Candida albicans*, maintained on Sabouraud dextrose agar plates. The fungus *Candida albicans* used in these assays is a clinical isolate from Columbia Presbyterian Hospital, NY. A single colony is inoculated in Sabouraud dextrose broth and cultured for 16–18 hrs at 37° C. An aliquot of the overnight culture is inoculated in fresh broth and grown for 3 hrs to a density of $7 \times 10^6$/ml as determined with a counting chamber. The fungus culture is diluted to a final concentration of $2 \times 10^4$ CFU/ml in 10 mM sodium phosphate buffer, pH 5.5 and this suspension is incubated for 3 hrs with hemoglobin or its α or β chains in NaPB pH 5.5. Aliquots are diluted 1:10 in M63 minimal media and spread onto Sabouraud dextrose agar plates to determine surviving CFU after 20 hrs at 37° C.

B. Radial diffusion assay

The fungus is grown for 3 hrs from an overnight culture in Sabouraud dextrose broth, centrifuged at 10,000 g for 10 min, washed twice in NaPB pH 5.5, and resuspended in NaPB (pH 5.5) at a final concentration of $4 \times 10^7$/ml. A 0.1 ml aliquot of this fungal suspension ($4 \times 10^6$ CFU) is added to 10 ml of autoclaved and cooled to (42° C.) NaPB pH 5.5 containing 1% w/v of low electroendosmosis type agarose (Sigma). After mixing the fungus in, the agar is poured into Lab-Tek square Petri dishes to form a uniform 1 mm thick layer. Wells with a 3 mm diameter are punched in and filled with 5 $\mu$l of control or sample, the plates are incubated for 3 hrs at 37° C. and overlaid with 10 ml of sterile agar maintained at 42° C. The overlay agar is 2× Sabouraud agar. After incubation of 18–24 hrs at 37° C., the diameter of the clear zone surrounding the wells containing an antifungal agent is measured.

Antimicrobial Activity of Pentides

Measurement of the antimicrobial activity of human hemoglobin, its heme-free α and β chains, CNBr-derived fragments of the α and β chains, and synthetic peptides derived therefrom were determined by radial diffusion assay and in some cases by plate assay. For the data provided in FIGS. 1–15, the ordinate shows the diameter of the clear zone expressed in arbitrary units where ten units=1.0 mm (23). The abcissa shows protein concentration in $\mu$g/ml. MIC is estimated by linear extrapolation of data points to an intercept with the x axis.

Each assay was performed with 3 experimental runs except where indicated. The radial diffusion assay is reliable and gives consistent results when used with the purified or semipurified compositions of the invention. The assay method was patterned after that of Lee et al (23).

Example 1

Antimicrobial activity for human hemoglobin was demonstrated by radial diffusion assay and is summarized in Table 1, Example 1 and in FIGS. 1 through 6.

Example 2

Antimicrobial activity for human hemoglobin was demonstrated by plate assay and provided the following data. The $IC_{50}$ for *Candida albicans* is in the range of 5 to 6 µg/ml and for *E. coli* is in the range of 8 to 10 µg/ml. $IC_{50}$ is expressed as the protein concentration required to kill 50% of the test organisms (i.e., 50% decrease in colony forming units).

Examples 3 and 4

Antimicrobial activity for the heme-free α chain of hemoglobin is summarized in Table 1, Example 3 antimicrobial activity for the heme-free β chain of hemoglobin is summarized in Table 1, Example 4.

Example 5

Antimicrobial activity for α and β chains of human hemoglobin was demonstrated by plate assay and provided the following data. The $IC_{50}$ values for the a chain were 4 to 5 µg/ml for Candida albicans and 15 to 20 µg/ml for *Escherichia coli*. The $IC_{50}$ values for the β chain were 4 to 5 µg/ml for *Candida albicans* and 10 to 15 µg/ml for *Escherichia coli*.

TABLE 1

ANTIMICROBIAL ACTIVITY
Radial Diffusion Assays
Human Hemoglobin and heme-free α and β Subunits
Minimum Inhibitory Concentration (MIC) in µg/ml

| Microorganism | Hemoglobin Example 1 pH 5.5 | Hemoglobin Example 1 pH 7.4 | α chains Example 3 pH 5.5 | α chains Example 3 pH 7.4 | β chains Example 4 pH 5.5 | β chains Example 4 pH 7.4 |
|---|---|---|---|---|---|---|
| Candida albicans | 50–70 | NT | 7 | NT | >50 | NT |
| Escherichia coli | 1–5 | 35–100 | 1–2 | — | 1.5–5 | 10–30 |
| Staphylococcus aureus | 4–6 | — | 300 | NT | 10 | NT |
| Pseudomonas aeruginosa | 5 | 50 | 50 | NT | 40–60 | NT |
| Streptococcus faecalis | 200–1000 | — | 3* | NT | 20 | NT |

Lack of effect indicated by (—)
NT = not tested
*Single experimental run

Examples 6–10

Antimicrobial activity for the CNBr cleavage fragments of the heme-free α and β chains is described in Table 2, Examples 6–10. Examples 6, 7 and 8 correspond to the α-1, α-2 and α-3 CNBr cleavage fragments, respectively and Examples 9 and 10 correspond to the β-1 and β-2 CNBr cleavage fragments, respectively. The data demonstrate that the α-3 (SEQ. ID.NO: 3) and β-2 (SEQ. ID.NO: 2) fragments are the most active.

TABLE 2

ANTIMICROBIAL ACTIVITY
Radial Diffusion Assays
CNBr Cleavage Products of Human Hemoglobin Heme-Free α and β Chains
Minimum Inhibitory Concentration (MIC) in µg/ml

| MICROORGANISM | α-1 Example 6 | α-2 Example 7 | α-3 Example 8 | β-1 Example 9 | β-2 Example 10 |
|---|---|---|---|---|---|
| Escherichia coli | >100 | >100 | 5–8 | >100 | 5 |
| Candida albicans | NT | NT | 10–50 | 25 | 25 |
| Streptococcus faecalis | 100 | NT | 7 | >50 | 8 |

NT = Not Tested

Examples 11 and 12

Synthetic peptides I and II (SEQ. ID NOS. 5 and 6, respectively) were synthesized by Protein Chemistry Core Facility in Howard Hughes Medical Institute at Columbia University according to conventional means. Antimicrobial activity of the synthetic peptides I (SEQ. ID.NO: 5) and II (SEQ. ID.NO: 6) is shown in Table 3, Examples 11 and 12, respectively.

TABLE 3

Radial Diffusion Assays
Assay Results of Two Synthetic Peptides
Minimum Inhibitory Concentration (MIC) µg/mL

| Microorganism | Peptide I Example 11 | Peptide II Example 12 |
|---|---|---|
| E. Coli | 15 | 1.5 |
| C. albicans | 10 | 40 |

The foregoing examples demonstrate experiments performed and contemplated by the present inventors in making and carrying out the invention. It is believed that these examples include a disclosure of techniques which serve to demonstrate the practice of and usefulness of the invention. It will be appreciated by those skilled in the art that various changes may be made in the embodiments and techniques exemplified without departing from the scope of the invention.

REFERENCES:

1) Moberg C L, Cohn Z A (eds). 1990. Launching the antibiotic era. Personal accounts of the discovery and use of the first antibiotics. Rockefeller University Press, New York.
2) Sahl H-G. 1994. Gene enclosed antibiotics made in bacteria, in: Antimicrobial Peptides, Wiley, Chichester, pp 27–53.
3) Ganz T. 1994. Biosynthesis of defensins and other antimicrobial peptides, In: Antimicrobial Peptides, Wiley, Chichester, pp 63–37.
4) Zasloff M. 1987. Magainins, a class of antimicrobial peptides from Xenopus skin: isolation, characterization of two active forms and partial cDNA sequence of precursor. *Proc Natl Acad Sci* 84: 5449–5453.
5) Giovanni M G, Poulter L, Gibson B W, Williams D H. 1987. Biosynthesis and degradation of peptide derived from Xenopus Laevis prohormones. *Biochem J* 243:113–120.

6) Dizon R A, Dey P M, Lamb C J. 1983. Phytoalexins: enzymology and molecular biology. *Adv Enzymol Relat Areas of Mol Biol* 55: 1–135.
7) Stintzi A, Hertz T, Pradad V, et al. 1993. Plant pathogenesis-related proteins and their role in defense against pathogens. *Biochemie* 75: 687–706.
8) Hultmark D, Steiner H, Rasmulson T, Boman H C. 1980. insect immunity: purification and properties of three inducible bacteriocidal proteins from hemolymph of immunized pupae of Hylorphora cecropia. *Eur J Biochem* 106: 7–16.
9) Hultmark D. 1993. Immune reactions in Drosphila and other insects; a model for innate immunity. *Trends Genet* 9: 178–183.
10) Steiner H, Hultmark D, Engstrom A, Bennich H, Boman H G. 1981. Sequence and specificity of two antibacterial proteins involved in insect immunity. *Nature* 292: 245–248.
11) Natori S. 1990. Dual functions of insect immunity proteins in defense and development. *Res Immunol.* 141: 938–939.
12) Moore K S, Wohrli S, Roger H, et al. 1993. Squalamine; an aminosteriod antibiotic from the shark. *Proc Natl Acad Sci* 90: 1354–1358.
13) Kreil G. 1994. Antimicrobial peptides from amphibian skin; an overview, in, Antimicrobial Peptides, Ciba Foundations Symposium 186, pp 77–90. John Wiley & Sons, Chichester, N.Y.
14) Jacob L, Zasloff M. 1994. Potential therapeutic applications of magainins and other antimicrobial agents of animal origin, in Antimicrobial Peptides, John Wiley & Sons, Chichester, N.Y.
15) Nicolas P, Mor A. 1995. Peptides as weapons against microorganisms in the chemical defense system of vertebrates. *Ann Rev Microbiol* 49: 277–304.
16) Perutz M F. 1990. Mechanisms regulating the reactions of human hemoglobin with oxygen and carbon monoxide. *Annu Rev Physiol* 52:1–25, 1990.
17) Perutz M F. 1979. Regulation of oxygen affinity of hemoglobin: influence of structure of the globin on the heme. *Annu Rev Biochem* 48:327–386.
18) Ritter, S. K. 1998. Passing a Bood Test. Science/Technology, C&EN May 18, 1998:37–44.
19) Winslow, R. M. 1995. "Blood Substitutes: 1995 in the Literature" from *Blood Substitutes: Physiological Basis of Efficacy*, Chpater 1. Eds. Winslow, R. M. et al., Birkhäuser, Boston.
20) Christensen S M, Medina P, Winslow R W, Snell S M, Zegna A, Marini M A. 1988. Preparation of human hemoglobin Ao for possible use as a blood substitute. *J Biochem Biophys Method* 17:143–154.
21) Masala B, Manca L. 1994. Detection of globin chains by reversed-phase high-performance liquid chromatography. *Methods in Enzymology* 231:21–44.
22) Schagger H, von Jagow G. 1987. Tricine-sodium dodecyl sulphate-polyacrylamide gel electrophoresis for the separation of proteins in the range from 1 to 100 kDa. *Anal Biochem* 166:368–376.
23) Lee I H, Cho Y, Lehrer R I. 1997. Effects of pH and salinity on the antimicrobial properties of Clavanins. *Infections & Immunity* 65:2898–2903.

What is claimed is:

1. A method for killing bacteria or fungi, wherein said bacteria or fungi are selected from the group consisting of gram-negative bacteria, gram-positive bacteria and yeast, comprising contacting the bacteria or fungi with a bacterial or fungal cell killing effective amount of a fragment of mammalian hemoglobin protein, selected from the group consisting of mammalian heme-free hemoglobin α chain, a mammalian heme-free hemoglobin β chain, a mammalian hemoglobin α-3 fragment, a mammalian hemoglobin β-2 fragment, a peptide which is SEQ ID NO:3, a peptide which is SEQ ID NO:2, a peptide which is SEQ ID NO:5, a peptide which is SEQ ID NO:6; said mammalian hemoglobin protein fragment retaining bacterial or fungal killing function, wherein said contacting is for a time and under conditions effective to kill bacteria or fungi.

2. The method according to claim 1, wherein said hemoglobin protein, hemoglobin protein fragment or polypeptide fragments are derived from humans.

3. The method according to claim 1, wherein the bacteria are Gram-negative bacteria.

4. The method according to claim 3, wherein the Gram-negative bacteria are selected from the group consisting of *Escherichia coli* and *Pseudomonas aeruginosa*.

5. The method according to claim 1 wherein the bacteria are Gram-positive bacteria.

6. The method according to claim 5 wherein the Gram-positive bacteria are selected from the group consisting of *Staphylococcus aureus* and *Streptococcus faecalis*.

7. The method according to claim 1, wherein the fungi are *Candida albicans*.

8. A method for killing bacteria or fungi in a subject wherein said bacteria or fungi are selected from the group consisting of gram-negative bacteria, gram-positive bacteria and yeast, which comprises administering to the subject a bacterial or fungal cell killing effective amount of a fragment of mammalian hemoglobin protein, selected from the group consisting of a mammalian heme-free hemoglobin α chain, a mammalian heme-free hemoglobin β chain, a mammalian hemoglobin α-3 fragment, a mammalian hemoglobin β-2 fragment, a peptide which is SEQ ID NO:3, a peptide which is SEQ ID NO:2, a peptide which is SEQ ID NO:5, a peptide which is SEQ ID NO:6; wherein said mammalian hemoglobin protein fragment retains bacterial or fungal killing function; and, is administered topically for a time and under conditions effective to kill bacteria or fungi in a subject.

9. The method according to claim 8, wherein said hemoglobin protein, hemoglobin protein fragment or polypeptide fragments are derived from humans.

10. The method according to claim 8, wherein the bacteria are Gram-negative bacteria.

11. The method according to claim 10, wherein the Gram-negative bacteria are selected from the group consisting of *Escherichia coli* and *Pseudomonas aeruginosa*.

12. The method according to claim 8 wherein the bacteria are Gram-positive bacteria.

13. The method according to claim 12 wherein the Gram-positive bacteria are selected from the group consisting of *Staphylococcus aureus* and *Streptococcus faecalis*.

14. The method according to claim 8, wherein the fungi are *Candida albicans*.

15. A method for treating material subject to bacterial or fungal contamination, wherein said bacteria or fungi are selected from the group consisting of gram-negative bacteria, gram-positive bacteria and yeast comprising applying or admixing with said material a bacterial or fungal cell killing effective amount of a fragment of mammalian hemoglobin protein, selected from the group consisting of a mammalian heme-free hemoglobin α chain, a mammalian heme-free hemoglobin β chain, a mammalian hemoglobin α-3 fragment, a mammalian hemoglobin β-2 fragment, a peptide which is SEQ ID NO:3, a peptide which is SEQ ID NO:2, a peptide which is SEQ ID NO:5, a peptide which is SEQ ID NO:6; said mammalian hemoglobin fragment retaining bacterial or fungal killing function, wherein said applying or admixing is for a time and under conditions effective to treat bacteria or fungi in a material.

16. The method according to claim 15, wherein said hemoglobin protein, hemoglobin protein fragment or polypeptide fragments are derived from humans.

17. The method according to claim 15, wherein the bacteria are Gram-negative bacteria.

18. The method according to claim 17, wherein the Gram-negative bacteria are selected from the group consisting of *Escherichia coli* and *Pseudomonas aeruginosa*.

19. The method according to claim 15 wherein the bacteria are Gram-positive bacteria.

20. The method according to claim 19 wherein the Gram-positive bacteria are selected from the group consisting of *Staphylococcus aureus* and *Streptococcus faecalis*.

21. The method according to claim 15, wherein the fungi are *Candida albicans*.

22. A pharmaceutical dosage form comprising a bacterial or fungal cell killing effective amount of a fragment of mammalian hemoglobin protein, selected from the group consisting of a mammalian heme-free hemoglobin α chain, a mammalian heme-free hemoglobin β chain, a mammalian hemoglobin α-3 fragment, a mammalian hemoglobin β-2 fragment, a peptide which is SEQ ID NO:3, a peptide which is SEQ ID NO:2, a peptide which is SEQ ID NO:5, a peptide which is SEQ ID NO:6; and a pharmaceutically acceptable carrier, wherein said fragment of mammalian hemoglobin protein kills bacteria or fungi.

23. The pharmaceutical dosage form according to claim 22, wherein said hemoglobin protein, hemoglobin protein fragment or polypeptide fragments are derived from humans.

24. An isolated polypeptide fragment, which has a bacterial or fungal cell killing activity, consisting of a peptide which is SEQ ID NO:3, a peptide which is SEQ ID NO:2, a peptide which is SEQ ID NO:5, a peptide which is SEQ ID NO:6, a peptide which is SEQ ID NO:8, and a peptide which is SEQ ID NO:9.

25. A method for killing bacteria or fungi, wherein said bacteria or fungi are selected from the group consisting of gram-negative bacteria, gram-positive bacteria and yeast, comprising contacting the bacteria or fungi with a bacterial or fungal cell killing effective amount of a fragment of human hemoglobin protein, selected from the group consisting of a mammalian heme-free hemoglobin α chain, a mammalian heme-free hemoglobin β chain, a human hemoglobin α-3 fragment, a human hemoglobin β-2 fragment, a peptide which is SEQ ID NO:3, a peptide which is SEQ ID NO:2, a peptide which is SEQ ID NO:5, a peptide which is SEQ ID NO:6; said human hemoglobin protein fragment retaining bacterial or fungal killing function, wherein said contacting is for a time and under conditions effective to kill bacteria or fungi.

* * * * *